United States Patent
Ellis et al.

(10) Patent No.: US 10,703,814 B2
(45) Date of Patent: Jul. 7, 2020

(54) METHOD OF TREATMENT WITH HUMANIZED ANTI-IL-18 ANTIBODIES

(71) Applicant: Glaxo Group Limited, Brentford, Middlesex (GB)

(72) Inventors: Jonathan Henry Ellis, Stevenage (GB); Volker Germaschewski, Stevenage (GB); Paul Andrew Hamblin, Stevenage (GB)

(73) Assignee: Glaxo Group Limited (GB)

( * ) Notice: Subject to any disclaimer, the term of this patent is extended or adjusted under 35 U.S.C. 154(b) by 0 days.

(21) Appl. No.: 16/161,175

(22) Filed: Oct. 16, 2018

(65) Prior Publication Data

US 2019/0031753 A1    Jan. 31, 2019

Related U.S. Application Data

(60) Division of application No. 15/293,823, filed on Oct. 14, 2016, now abandoned, which is a continuation of application No. 14/133,751, filed on Dec. 19, 2013, now Pat. No. 9,499,617, which is a continuation of application No. 13/315,358, filed on Dec. 9, 2011, now Pat. No. 8,637,018, which is a continuation of application No. 11/752,707, filed on May 23, 2007, now Pat. No. 8,133,978.

(30) Foreign Application Priority Data

May 25, 2006  (GB) .................................. 0610438.4
Jun. 5, 2006   (GB) .................................. 0611046.4

(51) Int. Cl.
*A61K 39/395*  (2006.01)
*C07K 16/24*   (2006.01)
*A61K 39/00*   (2006.01)

(52) U.S. Cl.
CPC ............ *C07K 16/244* (2013.01); *A61K 39/00* (2013.01); *C07K 2317/24* (2013.01); *C07K 2317/565* (2013.01); *C07K 2317/567* (2013.01); *C07K 2317/76* (2013.01); *C07K 2317/92* (2013.01)

(58) Field of Classification Search
CPC .................................................... A61K 39/00
See application file for complete search history.

(56) References Cited

U.S. PATENT DOCUMENTS

| | | | |
|---|---|---|---|
| 6,197,297 B1 | 3/2001 | Kunikata et al. | |
| 6,509,449 B1 | 1/2003 | Kunikata et al. | |
| 6,706,487 B1 | 3/2004 | Abdel-Meguid et al. | |
| 2002/0128450 A1 | 9/2002 | Nishida et al. | |
| 2005/0100965 A1 | 5/2005 | Ghayur et al. | |
| 2005/0147610 A1 | 7/2005 | Ghayur et al. | |

FOREIGN PATENT DOCUMENTS

| | | |
|---|---|---|
| EP | 0 528 767 | 2/1993 |
| EP | 0 692 536 | 1/1996 |
| EP | 0 712 863 | 5/1996 |
| EP | 0 712 931 | 5/1996 |
| EP | 0 974 600 | 1/2000 |
| EP | 1 163 271 | 7/2008 |
| WO | WO 93/11237 | 6/1993 |
| WO | WO 1995/035375 | 12/1995 |
| WO | WO 99/09063 | 2/1999 |
| WO | WO2000/56771 | 9/2000 |
| WO | WO 2001/58956 | 8/2001 |
| WO | WO 2001/058956 | 8/2001 |
| WO | WO 2001/062285 | 8/2001 |
| WO | WO 2002/032374 | 4/2002 |
| WO | WO 2002/066063 | 8/2002 |
| WO | WO 2003/008452 | 1/2003 |
| WO | WO 2003/013577 | 2/2003 |
| WO | WO 2004/097019 | 11/2004 |
| WO | WO 2005/047307 | 5/2005 |
| WO | WO 2007/080174 | 7/2007 |
| WO | WO2007/096396 | 8/2007 |
| WO | WO2007/137984 | 12/2007 |
| WO | WO2010/20593 | 2/2010 |

OTHER PUBLICATIONS

Bombardieri, et al., "Interleukin-18 as a potential therapeutic target in chronic autoimmune/inflammatory conditions," *Expert Opin. Biol. Ther.*, vol. 7, No. 1, pp. 31-40 (2007).
Bonilla, et al., "Vκ Gene Usage, Idiotype Expression and Antigen Binding Among Clones Expressing the $V_H$X24 Gene Family Derived from Naive and Anti-Idiotype Immune Balb/c Mice[1]," *Journal of Immunology*, vol. 145, No. 2, pp. 616-622 (1990).
Chen et al., 1999, J. Molecular Biology, 293:865-881.
Dinarello, et al., "Overview of Interleukin-18: more than an interferon-γ inducing factor," *Journal of Leukocyte Biology*, vol. 63, pp. 658-664 (1998).
Holmes, et al., "Characterization of the In Vitro and In Vivo Activity of Monoclonal Antibodies to Human IL-18," *Hybridoma*, vol. 19, No. 5, pp. 363-367 (2000).
Johnstone et al., 1990, Molecular Immunology, 27:327-333.
Jones, et al., "Expression of TIMP3 mRNA is elevated in retinas affected by simplex retinitis pigmentosa," *FEBS Letters*, vol. 352, pp. 171-174 (1994).
Rekvig, et al., "Molecular Analyses of Anti-DNA Antibodies Induced by Polymavirus BK in BALB/c Mice," *Scand. Journal of Immunology*, vol. 41, No. 6, pp. 593-602 (1995).
Rosa, et al., "p619, a giant protein related to the chromosome condensation regulator RCC1, stimulates guanine nucleotide exchange on ARF1 and Rab proteins," *EMBO Journal*, vol. 15, No. 16, pp. 4262-4273 (1996).

(Continued)

*Primary Examiner* — Prema M Mertz
(74) *Attorney, Agent, or Firm* — Jason C. Fedon

(57) ABSTRACT

The present invention discloses humanised anti-IL-18 antibodies, methods of manufacture, and methods of treatment with said antibodies. Further disclosed are screening methods using for example surface plasmon resonance to identify antibodies with therapeutic potential.

13 Claims, 22 Drawing Sheets
Specification includes a Sequence Listing.

(56) References Cited

OTHER PUBLICATIONS

Taniguchi, et al.,"Characterization of anti-human interleukin-18 (IL-18)/interferon-γ-inducing factor (IGIF) monoclonal antibodies and their application in the measurement of human IL-18 by ELISA," *Journal of Immunological Methods*, vol. 206, pp. 107-113 (1997).

Taylor, et al., "Immunotherapy for rheumatoid arthritis," *Current Opinion in Immunology*, vol. 13, pp. 611-616 (2001).

Wildbaum, et al., "Neutralizing Antibodies to IFN-γ-Inducing Factor Prevent Experimental Autoimmune Encephalomyelitis[1]," *The Journal of Immunology*, vol. 161, pp. 6368-6374 (1998).

*KD of H1L1 & H1L2 Vs Hu IL18 at Various temperatures*

SEQUENCE LISTING

```
<160> NUMBER OF SEQ ID NOS: 40

<210> SEQ ID NO 1
<211> LENGTH: 5
<212> TYPE: PRT
<213> ORGANISM: Artificial Sequence
<220> FEATURE:
<223> OTHER INFORMATION: CDRH1

<400> SEQUENCE: 1

Gly Tyr Tyr Phe His
1               5

<210> SEQ ID NO 2
<211> LENGTH: 17
<212> TYPE: PRT
<213> ORGANISM: Artificial Sequence
<220> FEATURE:
<223> OTHER INFORMATION: CDRH2

<400> SEQUENCE: 2

Arg Ile Asp Pro Glu Asp Asp Ser Thr Lys Tyr Ala Glu Arg Phe Lys
1               5                   10                  15

Asp

<210> SEQ ID NO 3
<211> LENGTH: 17
<212> TYPE: PRT
<213> ORGANISM: Artificial Sequence
<220> FEATURE:
<223> OTHER INFORMATION: CDRH3

<400> SEQUENCE: 3

Trp Arg Ile Tyr Arg Asp Ser Ser Gly Arg Pro Phe Tyr Val Met Asp
1               5                   10                  15
```

Ala

<210> SEQ ID NO 4
<211> LENGTH: 11
<212> TYPE: PRT
<213> ORGANISM: Artificial Sequence
<220> FEATURE:
<223> OTHER INFORMATION: CDRL1

<400> SEQUENCE: 4

```
Leu Ala Ser Glu Asp Ile Tyr Thr Tyr Leu Thr
1               5                   10
```

<210> SEQ ID NO 5
<211> LENGTH: 7
<212> TYPE: PRT
<213> ORGANISM: Artificial Sequence
<220> FEATURE:
<223> OTHER INFORMATION: CDRL2

<400> SEQUENCE: 5

```
Gly Ala Asn Lys Leu Gln Asp
1               5
```

<210> SEQ ID NO 6
<211> LENGTH: 9
<212> TYPE: PRT
<213> ORGANISM: Artificial Sequence
<220> FEATURE:
<223> OTHER INFORMATION: CDRL3

<400> SEQUENCE: 6

```
Leu Gln Gly Ser Lys Phe Pro Leu Thr
1               5
```

<210> SEQ ID NO 7
<211> LENGTH: 193
<212> TYPE: PRT
<213> ORGANISM: Homo sapiens

<400> SEQUENCE: 7

```
Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
                20                  25                  30

Leu Glu Ser Asp Tyr Phe Gly Lys Leu Glu Ser Lys Leu Ser Val Ile
            35                  40                  45

Arg Asn Leu Asn Asp Gln Val Leu Phe Ile Asp Gln Gly Asn Arg Pro
        50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
                100                 105                 110

Glu Asn Lys Ile Ile Ser Phe Lys Glu Met Asn Pro Pro Asp Asn Ile
            115                 120                 125

Lys Asp Thr Lys Ser Asp Ile Ile Phe Phe Gln Arg Ser Val Pro Gly
        130                 135                 140

His Asp Asn Lys Met Gln Phe Glu Ser Ser Ser Tyr Glu Gly Tyr Phe
145                 150                 155                 160
```

Leu Ala Cys Glu Lys Glu Arg Asp Leu Phe Lys Leu Ile Leu Lys Lys
            165                 170                 175

Gly Asp Glu Leu Gly Asp Arg Ser Ile Met Phe Thr Val Gln Asn Glu
        180                 185                 190

Asp

<210> SEQ ID NO 8
<211> LENGTH: 582
<212> TYPE: DNA
<213> ORGANISM: Homo sapiens

<400> SEQUENCE: 8

```
atggctgctg aaccagtaga agacaattgc atcaactttg tggcaatgaa atttattgac      60
aatacgcttt actttatagc tgaagatgat gaaaacctgg aatcagatta ctttggcaag     120
cttgaatcta aattatcagt cataagaaat ttgaatgacc aagttctctt cattgaccaa     180
ggaaatcggc tctatttgaa agatatgact gattctgact gtagagataa tgcaccccgg     240
accatattta ttataagtat gtataaagat agccagccta gaggtatggc tgtaactatc     300
tctgtgaagt gtgagaaaat ttcaactctc tcctgtgaga acaaaattat ttcctttaag     360
gaaatgaatc ctcctgataa catcaaggat acaaaaagtg acatcatatt ctttcagaga     420
agtgtcccag acatgataa taagatgcaa tttgaatctt catcatacga aggatacttt     480
ctagcttgtg aaaagagag agacctttt aaactcattt tgaaaaaga ggatgaattg     540 ggggatagat ctataatgtt cactgttcaa acgaagacta g                        582
```

<210> SEQ ID NO 9
<211> LENGTH: 456
<212> TYPE: PRT
<213> ORGANISM: Artificial Sequence
<220> FEATURE:
<223> OTHER INFORMATION: H1

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Val Ser Gly Glu Ile Ser Thr Gly Tyr
            20                  25                  30

Tyr Phe His Trp Val Arg Gln Ala Pro Gly Lys Gly Leu Glu Trp Met
        35                  40                  45

Gly Arg Ile Asp Pro Glu Asp Ser Thr Lys Tyr Ala Glu Arg Phe
    50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Thr Thr Trp Arg Ile Tyr Arg Asp Ser Ser Gly Arg Pro Phe Tyr Val
        100                 105                 110

Met Asp Ala Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

```
His Thr Phe Pro Ala Val Leu Gln Ser Ser Gly Leu Tyr Ser Leu Ser
            180                 185                 190
Ser Val Val Thr Val Pro Ser Ser Leu Gly Thr Gln Thr Tyr Ile
        195                 200                 205
Cys Asn Val Asn His Lys Pro Ser Asn Thr Lys Val Asp Lys Lys Val
    210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
    290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Asp Glu Leu Thr
        355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
        435                 440                 445
Ser Leu Ser Leu Ser Pro Gly Lys
    450                 455

<210> SEQ ID NO 10
<211> LENGTH: 1371
<212> TYPE: DNA
<213> ORGANISM: Artificial Sequence
<220> FEATURE:
<223> OTHER INFORMATION: H1

<400> SEQUENCE: 10
caggtgcagc tggtgcagag cggagccgag gtgaagaagc tggcgccag cgtcaaggtg      60 tcctgtaagg tgtccggcga gatcagcacc ggctactact ccactgggt gaggcaggcc     120 cctggcaagg gcctggagtg gatgggcaga atcgaccccg aggacgacag caccaagtac     180
gccgagcggt tcaaggacag ggtgaccatg accgaggaca ccagcaccga taccgcctac     240
atggagctgt ccagcctgag aagcgaggat accgccgtgt actactgtac cactggcgg      300 atctacagag acagcagcgg cagacccttc tacgtgatgg atgcctgggg ccagggcaca     360
ctagtgaccg tgtccagcgc cagcaccaag ggcccagcg tgttccccct ggccccagc     420 agcaagagca ccagcggcgg cacagccgcc ctgggctgcc tggtgaagga ctacttcccc     480
```

```
gaaccggtga ccgtgtcctg aacagcgga gccctgacca gcggcgtgca caccttcccc    540
gccgtgctgc agagcagcgg cctgtacagc ctgagcagcg tggtgaccgt gcccagcagc    600
agcctgggca cccagaccta catctgtaac gtgaaccaca agcccagcaa caccaaggtg    660
gacaagaagg tggagcccaa gagctgtgac aagacccaca cctgcccccc ctgccctgcc    720
cccgagctgc tgggaggccc cagcgtgttc ctgttccccc caagcctaa ggacaccctg     780 atgatcagca gaaccccga ggtgacctgt gtggtggtgg atgtgagcca cgaggaccct     840
gaggtgaagt tcaactggta cgtggacggc gtggaggtgc acaatgccaa gaccaagccc    900
agggaggagc agtacaacag cacctaccgg gtggtgtccg tgctgaccgt gctgcaccag    960
gattggctga acggcaagga gtacaagtgt aaggtgtcca acaaggccct gcctgcccct   1020
atcgagaaaa ccatcagcaa ggccaagggc cagcccagag agccccaggt gtacaccctg   1080 cccccctagca gagatgagct gaccaagaac caggtgtccc tgacctgcct ggtgaagggc   1140
ttctacccca gcgacatcgc cgtggagtgg gagagcaacg gccagcccga gaacaactac   1200
aagaccaccc cccctgtgct ggacagcgat ggcagcttct tcctgtacag caagctgacc   1260
gtggacaaga gcagatggca gcagggcaac gtgttcagct gctccgtgat gcacgaggcc   1320
ctgcacaatc actacaccca gaagagcctg agcctgtccc tggcaagtg a              1371
```

<210> SEQ ID NO 11
<211> LENGTH: 126
<212> TYPE: PRT
<213> ORGANISM: Artificial Sequence
<220> FEATURE:
<223> OTHER INFORMATION: H1 variable region

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Val Ser Gly Glu Ile Ser Thr Gly Tyr
            20                  25                  30

Tyr Phe His Trp Val Arg Gln Ala Pro Gly Lys Gly Leu Glu Trp Met
        35                  40                  45

Gly Arg Ile Asp Pro Glu Asp Asp Ser Thr Lys Tyr Ala Glu Arg Phe
    50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Thr Trp Arg Ile Tyr Arg Asp Ser Ser Gly Arg Pro Phe Tyr Val
            100                 105                 110

Met Asp Ala Trp Gly Gln Gly Thr Leu Val Thr Val Ser Ser
        115                 120                 125
```

<210> SEQ ID NO 12
<211> LENGTH: 378
<212> TYPE: DNA
<213> ORGANISM: Artificial Sequence
<220> FEATURE:
<223> OTHER INFORMATION: H1 variable region

<400> SEQUENCE: 12

```
caggtgcagc tggtgcagag cggagccgag gtgaagaagc ctggcgccag cgtcaaggtg     60
tcctgtaagg tgtccggcga gatcagcacc ggctactact tccactgggt gaggcaggcc    120
```

```
cctggcaagg gcctggagtg gatgggcaga atcgacccsg aggacgacag caccaagtac      180
gccgagcggt tcaaggacag ggtgaccatg accgaggaca ccagcaccga taccgcctac      240
atggagctgt ccagcctgag aagcgaggat accgccgtgt actactgtac cacctggcgg      300
atctacagag acagcagcgg cagacccttc tacgtgatgg atgcctgggg ccagggcaca      360
ctagtgaccg tgtccagc                                                    378
```

<210> SEQ ID NO 13
<211> LENGTH: 214
<212> TYPE: PRT
<213> ORGANISM: Artificial Sequence
<220> FEATURE:
<223> OTHER INFORMATION: L2

<400> SEQUENCE: 13

```
Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Tyr Thr Tyr
            20                  25                  30

Leu Thr Trp Tyr Gln Gln Lys Pro Gly Lys Ala Pro Lys Leu Leu Ile
        35                  40                  45

Tyr Gly Ala Asn Lys Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Gly Ser Lys Phe Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 14
<211> LENGTH: 642
<212> TYPE: DNA
<213> ORGANISM: Artificial Sequence
<220> FEATURE:
<223> OTHER INFORMATION: L2

<400> SEQUENCE: 14

```
gatatccaga tgacccagtc ccccagcagc gtgtccgcct ctgtgggcga tagagtgacc      60
atcacctgcc tggccagcga ggacatctac acctacctga cctggtatca gcagaagcct     120
ggcaaggccc ctaagctgct gatctacggc gccaacaagc tgcaggacgg cgtgcccagc     180
agattcagcg gcagcggctc cggcaccgac tacaccctga ccatcagcag cctgcagcct     240
```

```
gaggatttcg ccacctacta ctgcctgcag ggcagcaagt tcccccctgac cttcggccag    300 ggcaccaagc tggagatcaa gcgtacggtg gccgccccca gcgtgttcat cttcccccca    360
agcgatgagc agctgaagag cggcaccgcc agcgtggtgt gtctgctgaa caacttctac    420 ccccggggagg ccaaggtgca gtggaaggtg gacaatgccc tgcagagcgg caacagccag    480
gagagcgtga ccgagcagga cagcaaggac tccacctaca gcctgagcag caccctgacc    540
ctgagcaagg ccgactacga aagcacaag gtgtacgcct gtgaggtgac ccaccagggc     600
ctgtccagcc ccgtgaccaa gagcttcaac cggggcgagt gc                        642
```

<210> SEQ ID NO 15
<211> LENGTH: 107
<212> TYPE: PRT
<213> ORGANISM: Artificial Sequence
<220> FEATURE:
<223> OTHER INFORMATION: L2 variable region

<400> SEQUENCE: 15

```
Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Tyr Thr Tyr
            20                  25                  30

Leu Thr Trp Tyr Gln Gln Lys Pro Gly Lys Ala Pro Lys Leu Leu Ile
        35                  40                  45

Tyr Gly Ala Asn Lys Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Gly Ser Lys Phe Pro Leu
                85                  90                  95

Thr Phe Gly Gln Gly Thr Lys Leu Glu Ile Lys
            100                 105
```

<210> SEQ ID NO 16
<211> LENGTH: 321
<212> TYPE: DNA
<213> ORGANISM: Artificial Sequence
<220> FEATURE:
<223> OTHER INFORMATION: L2 variable region

<400> SEQUENCE: 16

```
gatatccaga tgacccagtc ccccagcagc gtgtccgcct ctgtgggcga tagagtgacc    60
atcacctgcc tggccagcga ggacatctac acctacctga cctggtatca gcagaagcct    120
ggcaaggccc ctaagctgct gatctacggc gccaacaagc tgcaggacgg cgtgcccagc    180
agattcagcg gcagcggctc cggcaccgac tacaccctga ccatcagcag cctgcagcct    240
gaggatttcg ccacctacta ctgcctgcag ggcagcaagt tcccccctgac cttcggccag    300 ggcaccaagc tggagatcaa g                                              321
```

<210> SEQ ID NO 17
<211> LENGTH: 456
<212> TYPE: PRT
<213> ORGANISM: Artificial Sequence
<220> FEATURE:
<223> OTHER INFORMATION: H2

<400> SEQUENCE: 17

```
Gln Val Gln Leu Val Gln Ser Gly Ala Glu Val Lys Lys Pro Gly Ala
```

-continued

```
1               5                   10                  15
Ser Val Lys Val Ser Cys Lys Val Ser Gly Glu Ile Ser Thr Gly Tyr
                20                  25                  30

Tyr Phe His Trp Val Arg Arg Pro Gly Lys Gly Leu Glu Trp Met
            35                  40                  45

Gly Arg Ile Asp Pro Glu Asp Ser Thr Lys Tyr Ala Glu Arg Phe
        50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Thr Trp Arg Ile Tyr Arg Asp Ser Ser Gly Arg Pro Phe Tyr Val
            100                 105                 110

Met Asp Ala Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430
```

Ser Cys Ser Val Met His Glu Ala Leu His Asn His Tyr Thr Gln Lys
            435                 440                 445

Ser Leu Ser Leu Ser Pro Gly Lys
    450                 455

<210> SEQ ID NO 18
<211> LENGTH: 1368
<212> TYPE: DNA
<213> ORGANISM: Artificial Sequence
<220> FEATURE:
<223> OTHER INFORMATION: H2

<400> SEQUENCE: 18
caggtccagc tggtacagtc tggggctgag gtgaagaagc ctggggcctc agtgaaggtc      60
tcctgcaagg tttccggaga ataagtact ggatactatt ccactgggt gcgacgaagg      120
cctggaaaag ggcttgagtg gatgggaagg attgatcctg aggatgatag tactaaatat    180
gctgagaggt tcaaagacag agtcaccatg accgaggaca catctacaga cacagcctac    240
atggagctga gcagcctgag atctgaggac acggccgtgt attactgtac cacatggcgg    300
atataccgag atagttctgg ccgccccttc tatgttatgg atgcctgggg ccaagggaca    360
ctagtcacag tctcctcagc ctccaccaag ggcccatcgg tcttccccct ggcaccctcc    420
tccaagagca cctctggggg cacagcggcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagaaag ttgagcccaa atcttgtgac aaaactcaca catgcccacc gtgcccagca    720
cctgaactcc tggggggacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgt gtggtcagcg tcctcaccgt cctgcaccag    960
gactggctga atggcaagga gtacaagtgc aaggtctcca acaaagccct cccagccccc   1020
atcgagaaaa ccatctccaa agccaaaggg cagccccgag aaccacaggt gtacaccctg   1080
cccccatccc gggatgagct gaccaagaac caggtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctacag caagctcacc   1260
gtggacaaga gcaggtggca gcagggggaac gtcttctcat gctccgtgat gcatgaggct   1320
ctgcacaacc actacacgca gaagagcctc tccctgtctc cgggtaaa               1368

<210> SEQ ID NO 19
<211> LENGTH: 126
<212> TYPE: PRT
<213> ORGANISM: Artificial Sequence
<220> FEATURE:
<223> OTHER INFORMATION: H2 variable region

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Val Ser Gly Glu Ile Ser Thr Gly Tyr
            20                  25                  30

```
Tyr Phe His Trp Val Arg Arg Pro Gly Lys Gly Leu Glu Trp Met
         35                  40                  45

Gly Arg Ile Asp Pro Glu Asp Ser Thr Lys Tyr Ala Glu Arg Phe
 50                  55                  60

Lys Asp Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Thr Thr Trp Arg Ile Tyr Arg Asp Ser Ser Gly Arg Pro Phe Tyr Val
             100                 105                 110

Met Asp Ala Trp Gly Gln Gly Thr Leu Val Thr Val Ser Ser
             115                 120                 125
```

<210> SEQ ID NO 20
<211> LENGTH: 378
<212> TYPE: DNA
<213> ORGANISM: Artificial Sequence
<220> FEATURE:
<223> OTHER INFORMATION: H2 variable region

<400> SEQUENCE: 20

```
caggtccagc tggtacagtc tggggctgag gtgaagaagc ctggggcctc agtgaaggtc      60
tcctgcaagg tttccggaga ataagtact ggatactatt tccactgggt gcgacgaagg     120
cctggaaaag ggcttgagtg gatgggaagg attgatcctg aggatgatag tactaaatat     180
gctgagaggt tcaaagacag agtcaccatg accgaggaca catctacaga cacagcctac     240
atggagctga gcagcctgag atctgaggac acggccgtgt attactgtac cacatggcgg     300
atataccgag atagttctgg ccgcccttc tatgttatgg atgcctgggg ccaagggaca     360
ctagtcacag tctcctca                                                  378
```

<210> SEQ ID NO 21
<211> LENGTH: 456
<212> TYPE: PRT
<213> ORGANISM: Artificial Sequence
<220> FEATURE:
<223> OTHER INFORMATION: H3

<400> SEQUENCE: 21

```
Gln Val Gln Leu Val Gln Ser Gly Ala Glu Val Lys Lys Pro Gly Ala
 1               5                   10                  15

Ser Val Lys Val Ser Cys Lys Val Ser Gly Glu Ile Ser Thr Gly Tyr
             20                  25                  30

Tyr Phe His Phe Val Arg Arg Pro Gly Lys Gly Leu Glu Trp Met
         35                  40                  45

Gly Arg Ile Asp Pro Glu Asp Ser Thr Lys Tyr Ala Glu Arg Phe
 50                  55                  60

Lys Asp Arg Val Thr Met Thr Ala Asp Thr Ser Thr Asp Thr Ala Tyr
 65                  70                  75                  80

Met Glu Leu Ser Ser Leu Arg Ser Glu Asp Thr Ala Thr Tyr Phe Cys
                 85                  90                  95

Thr Thr Trp Arg Ile Tyr Arg Asp Ser Ser Gly Arg Pro Phe Tyr Val
             100                 105                 110

Met Asp Ala Trp Gly Gln Gly Thr Leu Val Thr Val Ser Ser Ala Ser
             115                 120                 125

Thr Lys Gly Pro Ser Val Phe Pro Leu Ala Pro Ser Ser Lys Ser Thr
         130                 135                 140
```

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
        180                 185                 190

Ser Val Val Thr Val Pro Ser Ser Leu Gly Thr Gln Thr Tyr Ile
    195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 22
<211> LENGTH: 1368
<212> TYPE: DNA
<213> ORGANISM: Artificial Sequence
<220> FEATURE:
<223> OTHER INFORMATION: H3

<400> SEQUENCE: 22
caggtccagc tggtacagtc tggggctgag gtgaagaagc ctggggcctc agtgaaggtc      60
tcctgcaagg tttccggaga ataagtact ggatactatt ccactttgt gcgacgaagg      120 cctggaaaag gcttgagtg gatgggaagg attgatcctg aggatgatag tactaaatat      180
gctgagaggt tcaaagacag agtcaccatg accgcagaca catctacaga cacagcctac      240
atggagctga gcagcctgag atctgaggac acggccactt attttgtac cacatggcgg      300

```
atataccgag atagttctgg ccgccccttc tatgttatgg atgcctgggg ccaagggaca      360
ctagtcacag tctcctcagc ctccaccaag ggcccatcgg tcttccccct ggcaccctcc      420
tccaagagca cctctggggg cacagcggcc ctgggctgcc tggtcaagga ctacttcccc      480
gaaccggtga cggtgtcgtg gaactcaggc gccctgacca gcggcgtgca caccttcccg      540
gctgtcctac agtcctcagg actctactcc ctcagcagcg tggtgaccgt gccctccagc      600
agcttgggca cccagaccta catctgcaac gtgaatcaca agcccagcaa caccaaggtg      660
gacaagaaag ttgagcccaa atcttgtgac aaaactcaca catgcccacc gtgcccagca      720
cctgaactcc tggggggacc gtcagtcttc ctcttccccc caaaacccaa ggacaccctc      780
atgatctccc ggacccctga ggtcacatgc gtggtggtgg acgtgagcca cgaagaccct      840
gaggtcaagt tcaactggta cgtggacggc gtggaggtgc ataatgccaa gacaaagccg      900
cgggaggagc agtacaacag cacgtaccgt gtggtcagcg tcctcaccgt cctgcaccag      960
gactggctga atggcaagga gtacaagtgc aaggtctcca acaaagccct cccagccccc     1020
atcgagaaaa ccatctccaa agccaaaggg cagccccgag aaccacaggt gtacaccctg     1080
cccccatccc gggatgagct gaccaagaac caggtcagcc tgacctgcct ggtcaaaggc     1140
ttctatccca gcgacatcgc cgtggagtgg gagagcaatg ggcagccgga gaacaactac     1200
aagaccacgc ctcccgtgct ggactccgac ggctccttct tcctctacag caagctcacc     1260
gtggacaaga gcaggtggca gcaggggaac gtcttctcat gctccgtgat gcatgaggct     1320
ctgcacaacc actacacgca gaagagcctc tccctgtctc cgggtaaa                  1368
```

<210> SEQ ID NO 23
<211> LENGTH: 126
<212> TYPE: PRT
<213> ORGANISM: Artificial Sequence
<220> FEATURE:
<223> OTHER INFORMATION: H3 variable region

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Val Ser Gly Glu Ile Ser Thr Gly Tyr
            20                  25                  30

Tyr Phe His Phe Val Arg Arg Arg Pro Gly Lys Gly Leu Glu Trp Met
        35                  40                  45

Gly Arg Ile Asp Pro Glu Asp Asp Ser Thr Lys Tyr Ala Glu Arg Phe
    50                  55                  60

Lys Asp Arg Val Thr Met Thr Ala Asp Thr Ser Thr Asp Thr Ala Tyr
65                  70                  75                  80

Met Glu Leu Ser Ser Leu Arg Ser Glu Asp Thr Ala Thr Tyr Phe Cys
                85                  90                  95

Thr Thr Trp Arg Ile Tyr Arg Asp Ser Ser Gly Arg Pro Phe Tyr Val
            100                 105                 110

Met Asp Ala Trp Gly Gln Gly Thr Leu Val Thr Val Ser Ser
        115                 120                 125
```

<210> SEQ ID NO 24
<211> LENGTH: 378
<212> TYPE: DNA
<213> ORGANISM: Artificial Sequence
<220> FEATURE:
<223> OTHER INFORMATION: H3 variable region

<400> SEQUENCE: 24

```
caggtccagc tggtacagtc tggggctgag gtgaagaagc ctggggcctc agtgaaggtc    60
tcctgcaagg tttccggaga aataagtact ggatactatt ccactttgt gcgacgaagg    120
cctggaaaag ggcttgagtg gatgggaagg attgatcctg aggatgatag tactaaatat    180
gctgagaggt tcaaagacag agtcaccatg accgcagaca catctacaga cacagcctac    240
atggagctga gcagcctgag atctgaggac acggccactt attttgtac acatggcgg    300
atataccgag atagttctgg ccgccccttc tatgttatgg atgcctgggg ccaagggaca    360
ctagtcacag tctcctca                                                  378
```

<210> SEQ ID NO 25
<211> LENGTH: 214
<212> TYPE: PRT
<213> ORGANISM: Artificial Sequence
<220> FEATURE:
<223> OTHER INFORMATION: L1

<400> SEQUENCE: 25

```
Asp Ile Gln Met Thr Gln Ser Pro Ser Ser Val Ser Ala Ser Val Gly
1               5                   10                  15
Asp Arg Val Thr Ile Thr Cys Leu Ala Ser Glu Asp Ile Tyr Thr Tyr
            20                  25                  30
Leu Thr Trp Tyr Gln Gln Lys Pro Gly Lys Ala Pro Lys Leu Leu Ile
        35                  40                  45
Tyr Gly Ala Asn Lys Leu Gln Asp Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Leu Gln Gly Ser Lys Phe Pro Leu
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 26
<211> LENGTH: 642
<212> TYPE: DNA
<213> ORGANISM: Artificial Sequence
<220> FEATURE:
<223> OTHER INFORMATION: L1

<400> SEQUENCE: 26

```
gacatccaga tgacccagtc tccatcttct gtgtctgcat ctgtaggaga cagagtcacc    60
```

```
atcacttgtc tggcaagtga ggacatatac acttatttaa catggtatca gcagaaacca    120
gggaaagccc ctaagctcct gatctatggt gcaaataagt tgcaagatgg ggtcccatca    180
aggttcagcg gcagtggatc tgggacagat ttcactctca ctatcagcag cctgcagcct    240
gaagattttg caacttacta ttgtctacag ggttccaagt ttccgctcac gtttggccag    300
gggaccaagc tggagatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gacaacgccc tccaatcggg taactcccag    480
gagagtgtca cagagcagga cagcaaggac agcacctaca gcctcagcag caccctgacg    540
ctgagcaaag cagactacga aaacacaaa gtctacgcct gcgaagtcac ccatcagggc     600
ctgagctcgc ccgtcacaaa gagcttcaac aggggagagt gt    642
```

```
<210> SEQ ID NO 27
<211> LENGTH: 107
<212> TYPE: PRT
<213> ORGANISM: Artificial Sequence
<220> FEATURE:
<223> OTHER INFORMATION: L1 variable region

<400> SEQUENCE: 27
```

Asp Ile Gln Met Thr Gln Ser Pro Ser Val Ser Ala Ser Val Gly
1               5                   10                  15

Asp Arg Val Thr Ile Thr Cys Leu Ala Ser Glu Asp Ile Tyr Thr Tyr
            20                  25                  30

Leu Thr Trp Tyr Gln Gln Lys Pro Gly Lys Ala Pro Lys Leu Leu Ile
        35                  40                  45

Tyr Gly Ala Asn Lys Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Ser Lys Phe Pro Leu
                85                  90                  95

Thr Phe Gly Gln Gly Thr Lys Leu Glu Ile Lys
            100                 105

```
<210> SEQ ID NO 28
<211> LENGTH: 321
<212> TYPE: DNA
<213> ORGANISM: Artificial Sequence
<220> FEATURE:
<223> OTHER INFORMATION: L1 variable region

<400> SEQUENCE: 28
gacatccaga tgacccagtc tccatcttct gtgtctgcat ctgtaggaga cagagtcacc     60
atcacttgtc tggcaagtga ggacatatac acttatttaa catggtatca gcagaaacca    120
gggaaagccc ctaagctcct gatctatggt gcaaataagt tgcaagatgg ggtcccatca    180
aggttcagcg gcagtggatc tgggacagat ttcactctca ctatcagcag cctgcagcct    240
gaagattttg caacttacta ttgtctacag ggttccaagt ttccgctcac gtttggccag    300
gggaccaagc tggagatcaa a    321
```

```
<210> SEQ ID NO 29
<211> LENGTH: 214
<212> TYPE: PRT
<213> ORGANISM: Artificial Sequence
```

```
<220> FEATURE:
<223> OTHER INFORMATION: L3

<400> SEQUENCE: 29

Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Tyr Thr Tyr
            20                  25                  30

Leu Thr Trp Tyr Gln Gln Lys Pro Gly Lys Ala Pro Gln Leu Leu Ile
        35                  40                  45

Tyr Gly Ala Asn Lys Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Glu Gly Asp Tyr Tyr Cys Leu Gln Gly Ser Lys Phe Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 645
<212> TYPE: DNA
<213> ORGANISM: Artificial Sequence
<220> FEATURE:
<223> OTHER INFORMATION: L3

<400> SEQUENCE: 30
gacatccaga tgacccagtc tccatcttct gtgtctgcat ctgtaggaga cagagtcacc      60
atcacttgtc tggcaagtga ggacatatac acttatttaa catggtatca gcagaaacca    120
gggaaagccc ctcaactcct gatctatggt gcaaataagt tgcaagatgg ggtcccatca    180
aggttcagcg gcagtggatc tgggacagat tatactctca ctatcagcag cctgcagcct    240
gaagatgaag ggattactta ttgtctacag ggttccaagt tccgctcac gtttggccag    300 gggaccaagc tggagatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gacaacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 31
<211> LENGTH: 107
<212> TYPE: PRT
<213> ORGANISM: Artificial Sequence
<220> FEATURE:
<223> OTHER INFORMATION: L3 variable region

<400> SEQUENCE: 31

```
Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Tyr Thr Tyr
            20                  25                  30

Leu Thr Trp Tyr Gln Gln Lys Pro Gly Lys Ala Pro Gln Leu Leu Ile
        35                  40                  45

Tyr Gly Ala Asn Lys Leu Gln Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Glu Gly Asp Tyr Tyr Cys Leu Gln Gly Ser Lys Phe Pro Leu
                85                  90                  95

Thr Phe Gly Gln Gly Thr Lys Leu Glu Ile Lys
            100                 105
```

<210> SEQ ID NO 32
<211> LENGTH: 321
<212> TYPE: DNA
<213> ORGANISM: Artificial Sequence
<220> FEATURE:
<223> OTHER INFORMATION: L3 variable region

<400> SEQUENCE: 32

```
gacatccaga tgacccagtc tccatcttct gtgtctgcat ctgtaggaga cagagtcacc    60
atcacttgtc tggcaagtga ggacatatac acttatttaa catggtatca gcagaaacca   120
gggaaagccc ctcaactcct gatctatggt gcaaataagt tgcaagatgg ggtcccatca   180
aggttcagcg gcagtggatc tgggacagat tatactctca ctatcagcag cctgcagcct   240
gaagatgaag gggattacta ttgtctacag ggttccaagt tccgctcac gtttggccag   300 gggaccaagc tggagatcaa a                                             321
```

<210> SEQ ID NO 33
<211> LENGTH: 456
<212> TYPE: PRT
<213> ORGANISM: Artificial Sequence
<220> FEATURE:
<223> OTHER INFORMATION: 2c10 r.norvegicus h.sapiens IgG1 chimera

<400> SEQUENCE: 33

```
Glu Val Gln Leu Gln Gln Ser Gly Ala Glu Leu Val Arg Pro Gly Thr
1               5                   10                  15

Ser Val Lys Leu Ser Cys Lys Val Ser Gly Ile Ser Thr Gly Tyr
            20                  25                  30

Tyr Phe His Phe Val Arg Arg Pro Gly Gln Gly Leu Glu Trp Ile
        35                  40                  45

Gly Arg Ile Asp Pro Glu Asp Asp Ser Thr Lys Tyr Ala Glu Arg Phe
    50                  55                  60

Lys Asp Arg Ala Thr Leu Thr Ala Gln Thr Ser Ser Asn Thr Ala Tyr
65                  70                  75                  80

Leu Asn Leu Ser Ser Leu Thr Ser Glu Asp Thr Ala Thr Tyr Phe Cys
```

```
            85                  90                  95
Thr Thr Trp Arg Ile Tyr Arg Asp Ser Ser Gly Arg Pro Phe Tyr Val
            100                 105                 110

Met Asp Ala Trp Gly Gln Gly Thr Leu Val Thr Val Ser Ala Ser
            115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
            210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                    245                 250                 255

Lys Asp Thr Leu Met Ile Ser Arg Thr Pro Glu Val Thr Cys Val Val
                    260                 265                 270

Val Asp Val Ser His Glu Asp Pro Glu Val Lys Phe Asn Trp Tyr Val
                    275                 280                 285

Asp Gly Val Glu Val His Asn Ala Lys Thr Lys Pro Arg Glu Glu Gln
                    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                    325                 330                 335

Leu Pro Ala Pro Ile Glu Lys Thr Ile Ser Lys Ala Lys Gly Gln Pro
                    340                 345                 350

Arg Glu Pro Gln Val Tyr Thr Leu Pro Pro Ser Arg Asp Glu Leu Thr
                    355                 360                 365

Lys Asn Gln Val Ser Leu Thr Cys Leu Val Lys Gly Phe Tyr Pro Ser
                    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                    405                 410                 415

Ser Lys Leu Thr Val Asp Lys Ser Arg Trp Gln Gln Gly Asn Val Phe
                    420                 425                 430

Ser Cys Ser Val Met His Glu Ala Leu His Asn His Tyr Thr Gln Lys
                    435                 440                 445

Ser Leu Ser Leu Ser Pro Gly Lys
450                 455
```

<210> SEQ ID NO 34
<211> LENGTH: 1368
<212> TYPE: DNA
<213> ORGANISM: Artificial Sequence
<220> FEATURE:
<223> OTHER INFORMATION: 2c10 r.norvegicus h.sapiens IgG1 chimera

<400> SEQUENCE: 34

```
gaggtccagc tacagcagtc tggggctgag cttgtgagac ctgggacctc tgtgaagtta      60
tcttgcaaag tttctggcga aataagtaca ggatactatt tccactttgt gaggcgaagg     120
cctggacagg gtctggaatg gataggaagg attgatcctg aggatgatag tactaaatat     180
gctgagaggt tcaaagacag ggcgacgctc actgcacaaa catcctccaa cacagcctac     240
ctgaacctca gcagcctgac ctctgaggac actgcaactt attttgtac acatggcgg      300
atataccgag atagttctgg ccgccccttc tatgttatgg atgcctgggg tcaaggaaca     360
ctagtcacag tctcctcagc ctccaccaag ggcccatcgg tcttcccct ggcaccctcc      420
tccaagagca cctctggggg cacagcggcc ctgggctgcc tggtcaagga ctacttcccc     480
gaaccggtga cggtgtcgtg gaactcaggc gccctgacca gcggcgtgca ccttcccg      540
gctgtcctac agtcctcagg actctactcc ctcagcagcg tggtgaccgt gccctccagc     600
agcttgggca cccagaccta catctgcaac gtgaatcaca agcccagcaa caccaaggtg     660
gacaagaaag ttgagcccaa atcttgtgac aaaactcaca catgcccacc gtgcccagca     720
cctgaactcc tggggggacc gtcagtcttc ctcttcccc caaaacccaa ggacaccctc     780
atgatctccc ggacccctga ggtcacatgc gtggtggtgg acgtgagcca cgaagaccct     840
gaggtcaagt tcaactggta cgtggacggc gtggaggtgc ataatgccaa gacaaagccg     900
cgggaggagc agtacaacag cacgtaccgt gtggtcagcg tcctcaccgt cctgcaccag     960
gactggctga atggcaagga gtacaagtgc aaggtctcca acaaagccct cccagcccc     1020
atcgagaaaa ccatctccaa agccaaaggg cagccccgag aaccacaggt gtacaccctg     1080
cccccatccc gggatgagct gaccaagaac caggtcagcc tgacctgcct ggtcaaaggc     1140
ttctatccca gcgacatcgc cgtggagtgg gagagcaatg ggcagccgga gaacaactac     1200
aagaccacgc ctcccgtgct ggactccgac ggctccttct tcctctacag caagctcacc     1260
gtggacaaga gcaggtggca gcagggggaac gtcttctcat gctccgtgat gcatgaggct     1320
ctgcacaacc actacacgca gaagagcctc tccctgtctc cgggtaaa                  1368
```

<210> SEQ ID NO 35
<211> LENGTH: 214
<212> TYPE: PRT
<213> ORGANISM: Artificial Sequence
<220> FEATURE:
<223> OTHER INFORMATION: 2c10 r.norvegicus h.sapiens CKappa chimera

<400> SEQUENCE: 35

```
Asp Ile Gln Met Thr Gln Ser Pro Ala Ser Leu Ser Ala Ser Leu Gly
1               5                   10                  15
Glu Thr Val Ser Ile Glu Cys Leu Ala Ser Glu Asp Ile Tyr Thr Tyr
            20                  25                  30
Leu Thr Trp Tyr Gln Gln Lys Pro Gly Lys Ser Pro Gln Leu Leu Ile
        35                  40                  45
Tyr Gly Ala Asn Lys Leu Gln Asp Gly Val Pro Ser Arg Phe Ser Gly
    50                  55                  60
Ser Gly Ser Gly Thr Gln Tyr Ser Leu Lys Ile Ser Gly Ile Gln Pro
65                  70                  75                  80
Glu Asp Glu Gly Asp Tyr Phe Cys Leu Gln Gly Ser Lys Phe Pro Leu
                85                  90                  95
Thr Phe Gly Ser Gly Thr Lys Leu Glu Ile Lys Arg Thr Val Ala Ala
            100                 105                 110
```

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 36
<211> LENGTH: 642
<212> TYPE: DNA
<213> ORGANISM: Artificial Sequence
<220> FEATURE:
<223> OTHER INFORMATION: 2c10 r.norvegicus h.sapiens CKappa chimera

<400> SEQUENCE: 36

```
gacattcaaa tgacccagtc tccagcttcc ctgtctgcat ctctgggaga aactgtctcc      60
atcgaatgtc tggcaagtga ggacatatac acttatttaa catggtatca gcagaaacca    120
gggaaatctc ctcaactcct gatctatggt gcaaataagt tgcaagatgg ggtcccatca    180
cggttcagtg gcagtggatc tggcacacag tattctctca agatcagcgg catacaacct    240
gaagatgaag gggattattt ctgtctacag ggttccaagt ttccgctcac gttcggttct    300
gggaccaagc tggagatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gacaacgccc tccaatcggg taactcccag    480
gagagtgtca cagagcagga cagcaaggac agcacctaca gcctcagcag cacccctgacg    540
ctgagcaaag cagactacga aaacacaaa gtctacgcct gcgaagtcac ccatcagggc    600
ctgagctcgc ccgtcacaaa gagcttcaac aggggagagt gt                       642
```

<210> SEQ ID NO 37
<211> LENGTH: 98
<212> TYPE: PRT
<213> ORGANISM: Artificial Sequence
<220> FEATURE:
<223> OTHER INFORMATION: Heavy chain acceptor framework

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys

```
                     85                  90                  95
Ala Thr

<210> SEQ ID NO 38
<211> LENGTH: 95
<212> TYPE: PRT
<213> ORGANISM: Artificial Sequence
<220> FEATURE:
<223> OTHER INFORMATION: Light chain acceptor framework

<400> SEQUENCE: 38

Asp Ile Gln Met Thr Gln Ser Pro Ser Val Ser Ala Ser Val Gly
1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95

<210> SEQ ID NO 39
<211> LENGTH: 11
<212> TYPE: PRT
<213> ORGANISM: Artificial Sequence
<220> FEATURE:
<223> OTHER INFORMATION: JH6 sequence

<400> SEQUENCE: 39

Trp Gly Gln Gly Thr Leu Val Thr Val Ser Ser
1               5                  10

<210> SEQ ID NO 40
<211> LENGTH: 10
<212> TYPE: PRT
<213> ORGANISM: Artificial Sequence
<220> FEATURE:
<223> OTHER INFORMATION: Jkappa sequence

<400> SEQUENCE: 40

Phe Gly Gln Gly Thr Lys Leu Glu Ile Lys
1               5                  10
```

METHOD OF TREATMENT WITH HUMANIZED ANTI-IL-18 ANTIBODIES

This application is a divisional of U.S. application Ser. No. 15/293,823 filed on Oct. 14, 2016, which is a continuation of U.S. application Ser. No. 14/133,751 filed on Dec. 19, 2013, and issued as U.S. Pat. No. 9,499,617 on Nov. 22, 2016, which is a continuation of U.S. application Ser. No. 13/315,358 filed on Dec. 9, 2011 and issued as U.S. Pat. No. 8,637,018 on Jan. 28, 2014, which is a continuation of U.S. application Ser. No. 11/752,707 filed on May 23, 2007 and issued as U.S. Pat. No. 8,133,978 on Mar. 13, 2012, which claims priority to United Kingdom Application 0611046.4 filed on Jun. 5, 2006 and United Kingdom Application 0610438.4 filed on May 25, 2006, both of which are herein incorporated by reference.

FIELD OF THE INVENTION

The present invention relates generally to the field of immunoglobulins such as antibodies and in particular to humanised antibodies, useful in the treatment and diagnosis of conditions mediated by human interleukin-18.

BACKGROUND OF THE INVENTION

Human interleukin-18 (hIL-18) is a cytokine that is synthesized as a biologically inactive 193 amino acid precursor protein (Ushio, et al., *J. Immunol.* 156:4274, 1996). Cleavage of the precursor protein, for example by caspase-1 or caspase-4, liberates the 156 amino acid mature protein (Go, et al., *Science* 275:206, 1997; Ghayur, et al., *Nature* 386:619, 1997), which exhibits biological activities that include the costimulation of T cell proliferation, the enhancement of NK cell cytotoxicity, the induction of IFN-γ production by T cells and NK cells, and the potentiation of T helper type 1 (Th1) differentiation (Okamura, et al., *Nature* 378:88, 1995; Ushio, et al., *J. Immunol.* 156:4274, 1996; Micallef, et al., *Eur. J. Immunol.* 26:1647, 1996; Kohno, et al., *J. Immunol.* 158:1541, 1997; Zhang, et al., *Infect. Immunol.* 65:3594, 1997; Robinson, et al., *Immunity* 7:571, 1997). In addition, IL-18 is an efficacious inducer of human monocyte proinflammatory mediators, including IL-8, tumor necrosis factor-α (TNF-α), and prostaglandin E 2 (PGE 2) (Ushio, S., et al., J. Immunol. 156:4274-4279, 1996; Puren, A. J., et al., J. Clin. Invest. 10:711-721, 1997; Podolin, et al., *J. Immunol.* submitted, 1999).

The previously cloned IL-1 receptor-related protein (IL-1Rrp) (Parnet, et al., *J. Biol. Chem.* 271:3967, 1996) was identified as a subunit of the IL-18 receptor (Kd=18 nM) (Torigoe, et al., *J. Biol. Chem.* 272:25737, 1997). A second subunit of the IL-18 receptor exhibits homology to the IL-1 receptor accessory protein, and has been termed AcPL (for accessory protein-like). Expression of both IL-1 Rrp and AcPL are required for IL-18-induced NF-κB and JNK activation (Born, et al., *J. Biol. Chem.* 273:29445, 1998). In addition to NF-κB and JNK, IL-18 signals through IL-1 receptor-associated kinase (IRAK), p56lck (LCK), and mitogen-activated protein kinase (MAPK) (Micallef, et al., *Eur. J. Immunol.* 26:1647, 1996; Matsumoto, et al., *Biophys Biochem. Res. Comm.* 234:454, 1997; Tsuji-Takayama, et al., *Biochem. Biophys. Res. Comm.* 237:126, 1997).

TH1 cells, which produce proinflammatory cytokines such as IFN-γ, IL-2 and TNF-β (Mosmann, et al., *J. Immunol.* 136:2348, 1986), have been implicated in mediating many autoimmune diseases, including multiple sclerosis (MS), rheumatoid arthritis (RA), type 1, or insulin dependent, diabetes (IDDM), inflammatory bowel disease (IBD), and psoriasis (Mosmann and Sad, *Immunol. Today* 17:138, 1996). Thus, antagonism of a TH1-promoting cytokine such as IL-18 would be expected to inhibit disease development. Il-18 specific mAbs could be used as an antagonist.

The role of IL-18 in the development of autoimmune diseases has been demonstrated. Accordingly, it has been demonstrated that IL-18 expression is significantly increased in the pancreas and spleen of the nonobese diabetic (NOD) mouse immediately prior to the onset of disease (Rothe, et al., *J. Clin. Invest.* 99:469, 1997). Similarly, IL-18 levels have been shown to be markedly elevated in the synovial fluid of rheumatoid arthritis patients (Kawashima, et al., *Arthritis and Rheumatism* 39:598, 1996). Furthermore, it has been demonstrated that IL-18 administration increases the clinical severity of murine experimental allergic encephalomyelitis (EAE), a Th1-mediated autoimmune disease that is a model for multiple sclerosis. In addition, it has been shown that neutralizing anti-rat IL-18 antiserum prevents the development of EAE in female Lewis rats (Wildbaum, et al., *J. Immunol.* 161:6368, 1998). Accordingly, IL-18 is a desirable target for the development of a novel therapeutic for autoimmunity.

Taniguchi, et al., *J. Immunol. Methods* 206:107, describe seven murine and six rat anti-human IL-18 monoclonal antibodies (mAbs), which bind to four distinct antigenic sites. One of the murine mAbs (#125-2H), and the six rat mAbs inhibit IL-18-induced IFN-γ production by KG-1 cells, with the rat mAbs exhibiting neutralizing activities 10-fold lower than that of #125-2H. As demonstrated by Western blot analysis, three of the murine mAbs, but none of the rat mAbs, are strongly reactive with membrane-bound human IL-18. In addition, an enzyme-linked immunosorbent assay (ELISA) to detect human IL-18 is described, utilizing #125-2H and a rat mAb. The limit of detection of this ELISA is 10 pg/ml.

European patent application EP 0 712 931 discloses two mouse anti-human IL-18 mAbs, H1 (IgG1) and H2 (IgM). As demonstrated by Western blot analysis, both mAbs react with membrane-bound human IL-18, but not with membrane-bound human IL-12. H1 is utilized in an immunoaffinity chromatography protocol to purify human IL-18, and in an ELISA to measure human IL-18. H2 is utilized in a radioimmunoassay to measure human IL-18.

Neutralizing IL-18 antibodies may potentially be useful in relieving autoimmune diseases and related symptoms in man. Hence there is a need in the art for a high affinity IL-18 antagonist, such as a neutralizing monoclonal antibody to human interleukin 18, which would reduce Th1 cell differentiation and proliferation and thus autoimmune diseases and related symptoms.

SUMMARY OF THE INVENTION

Figure 1:
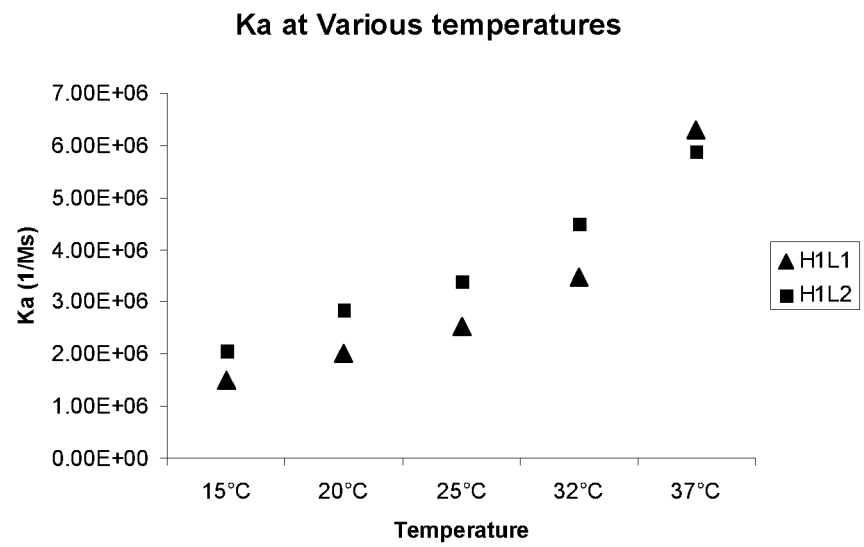
FIG. 1 shows the effect of temperature on the on-rate (ka) of H1L1 and H1L2.

In one aspect, the present invention provides a humanised anti-interleukin-18 antibody comprising a heavy chain and light chain having the following complementarity determining regions (CDRs):

CDRH1: SEQ ID NO:1;
CDRH2: SEQ ID NO:2;
CDRH3: SEQ ID NO:3;
CDRL1: SEQ ID NO:4;
CDRL2: SEQ ID NO:5; and
CDRL3: SEQ ID NO:6.

In a second aspect, the present invention provides a humanised anti-interleukin-18 antibody comprising a heavy chain and light chain having the following CDRs:

CDRH1: SEQ ID NO:1;
CDRH2: SEQ ID NO:2;
CDRH3: SEQ ID NO:3;
CDRL1: SEQ ID NO:4;
CDRL2: SEQ ID NO:5; and
CDRL3: SEQ ID NO:6 wherein the residue at position 71 of the light chain is substituted by the corresponding residue found in the donor antibody from which the CDRs are derived. It will be apparent to those skilled in the art that the term "derived" is intended to define not only the source in the sense of it being the physical origin for the material, but also the material that is structurally identical to the material, but which does not originate from the reference source. Thus, the corresponding residue "found in the donor antibody framework from which the CDRs are derived" need not necessarily be purified from the donor antibody framework. Similarly, CDRs "derived from a donor antibody" need not necessarily be purified from the donor antibody. CDRs and framework regions (FR) and numbering of amino acids follow, unless otherwise indicated, the Kabat definition as set forth in Kabat, et al., "Sequences of immunological interest", NIH.

In a third aspect, this invention provides a humanised anti-interleukin-18 antibody comprising CDRs derived from a donor antibody grafted onto a human acceptor framework which anti-interleukin 18 antibody comprises CDRs having the sequences set forth in SEQ ID NOs: 1, 2, 3, 4, 5, and 6, wherein the residue at position 71 of the light chain of said anti-interleukin-18 antibody is identical to the residue found in the corresponding position in the donor antibody framework.

In a fourth aspect, this invention provides a humanised anti-interleukin-18 antibody comprising CDRs having the sequences set forth in SEQ ID NOs: 1, 2, 3, 4, 5, and 6, wherein the antibody comprises a tyrosine at position 71 of the light chain.

In a fifth aspect, this invention provides a humanised anti-interleukin-18 antibody comprising a heavy chain having CDRs set forth in SEQ ID NOs: 1, 2, and 3, and a light chain having CDRs set forth in SEQ ID NOs: 4, 5, and 6, wherein said light chain CDRs are derived from a donor antibody having a tyrosine at position 71 of the donor antibody light chain.

In a sixth aspect, this invention provides a humanised anti-interleukin-18 antibody comprising CDRs from a donor antibody and a tyrosine at position 71 of the light chain of said humanised antibody, wherein the donor antibody is 2C10 or a framework variant thereof (i.e., the humanised antibody comprises the same CDRs but a different framework as 2C10. See U.S. Pat. No. 6,706,487).

In a seventh aspect, this invention provides a humanised anti-interleukin-18 antibody comprising:

(a) a heavy chain having CDRs with the sequences set forth in SEQ ID NOs:1, 2, and 3 grafted onto a human heavy chain acceptor framework; and (b) a light chain having CDRs with the sequences set forth in SEQ ID NOs: 4, 5, and 6 grafted onto a human light chain acceptor framework, wherein said human light chain acceptor framework comprises framework regions derived from SEQ ID NO: 38, wherein position 71 of SEQ ID NO: 38 is a tyrosine.

In an eighth aspect, this invention provides a humanised anti-interleukin-18 antibody comprising:

(a) a heavy chain having CDRs permissive of specific binding to human IL-18; and (b) a light chain comprising an acceptor framework and having CDRs with the sequences set forth in SEQ ID NOs: 4, 5, and 6 and having a tyrosine residue at position 71.

In one embodiment of the invention, the CDRs of the light chain are located at positions within the acceptor framework that correspond to the respective positions of the sequences set forth in SEQ ID NOs: 4, 5, and 6 within the sequence set forth in SEQ ID NO:35. In another embodiment of the invention, the light chain and/or the heavy chain are non-immunogenic in a human patient.

In a ninth aspect, this invention provides a humanised anti-interleukin-18 antibody comprising:

(a) a heavy chain comprising CDRs having sequences set forth in SEQ ID NO: 1, 2, and 3 and;

(b) a light chain comprising CDRs having sequences set forth in SEQ ID NO: 4, 5, and 6 grafted onto a human light chain acceptor framework, wherein said light chain acceptor framework of said humanised anti-interleukin-18 antibody comprises framework regions derived from a variant of the sequence set forth in SEQ ID NO:38, wherein said variant comprises a tyrosine at position 71, and wherein said variant comprises 75% or greater identity to the framework having the sequence set forth in SEQ ID NO:38. In another embodiment of the invention, said variant comprises 80% or greater, e.g., 81%, 82%, 83%, 84%, 85%, 86%, 87%, 88%, 89%, 90%, 91%, 92%, 93%, 94%, 95%, 96%, 97%, 98%, or 99% identity to the framework set forth in SEQ ID NO:38.

In a tenth aspect, this invention provides a humanised anti-interleukin-18 antibody, wherein said antibody comprises:

(a) CDRs set forth in SEQ ID NOs: 1, 2, 3, 4, 5, and 6 derived from a donor antibody, wherein said donor antibody comprises a tyrosine at position 71 of the donor antibody light chain;

(b) a human acceptor framework, wherein said acceptor framework comprises a phenylalanine at position 71 of the human light chain; and (c) wherein the anti-interleukin 18 antibody comprises a tyrosine at position 71 of the light chain.

In an eleventh aspect, this invention provides a humanised anti-interleukin-18 antibody comprising:

(a) CDRs set forth in SEQ ID NOs: 1, 2, 3, 4, 5, and 6 derived from a donor antibody, wherein said donor antibody comprises an aromatic amino acid at position 71 of the donor antibody light chain;

(b) a human acceptor framework, wherein said acceptor framework comprises at position 71 of the light chain acceptor framework a different type of aromatic amino acid from the aromatic amino acid in part (a); and (c) wherein the anti-interleukin-18 antibody comprises a light chain having at position 71 an aromatic amino acid derived from the antibody of part (a).

In a twelfth aspect, this invention provides a humanised anti-interleukin-18 antibody, wherein said antibody displays a equilibrium constant (KD) of 300 pM or less with respect to binding of human IL-18 when measured by surface plasmon resonance (e.g., Biacore™, using a Biacore™ 3000 instrument and conditions as set out in Example 4.a. below) at 37° C.).

In a thirteenth aspect, this invention provides a humanised anti-interleukin-18 antibody, wherein said antibody comprises CDRs as set forth in SEQ ID NO:1, 2, 3, 4, 5, and 6 and displays a equilibrium constant (KD) of 300 pM or less with respect to binding of human IL-18 when measured by surface plasmon resonance (e.g., using a Biacore™ 3000 instrument and conditions as set out in Example 4.a. below) at 37° C.

In one embodiment of the invention, the equilibrium constant (KD) of the antibody with respect to binding of human IL-18 when measured by surface plasmon resonance (preferably using a Biacore™ T100 instrument and conditions as set out in Example 4.b. below) at 37° C. is less than 90 pM. In other embodiments of the invention, the equilibrium constant is 70 pM or less, 65 pM, 60 pM, 55 pM, or 50 pM, or less.

In a fourteenth aspect, this invention provides a humanised anti-interleukin-18 antibody, wherein said antibody displays a dissociation constant or off-rate (kd) of 0.0002 1/s or less with respect to binding of human IL-18 when measured by surface plasmon resonance (e.g., Biacore™, using a Biacore™ T100 instrument and conditions as set out in Example 4.b. below) at 37° C.

In a fifteenth aspect, this invention provides a humanised anti-interleukin-18 antibody, wherein said antibody comprises:

(a) a heavy chain comprising CDRs derived from a donor antibody, which CDRs have sequences set forth in SEQ ID NOs: 1, 2, and 3 grafted onto a heavy chain acceptor framework, wherein said heavy chain acceptor framework comprises framework regions derived from the sequence set forth in SEQ ID NO: 37, wherein one or more residue/s of position/s 27, 28, 29, 93, 39, 40, 36, 71, 89, or 91 of the heavy chain is identical to the corresponding residue in the donor antibody heavy chain; and (b) a light chain comprising CDRs derived from a donor antibody which CDRs have sequences set forth in SEQ ID NO: 4, 5, and 6 grafted onto a light chain acceptor framework which light chain acceptor framework comprises framework regions derived from the sequence set forth in SEQ ID NO: 38, wherein position 71 and optionally one or more (e.g., all) residue/s of position/s 45, 83, 84, 85 of the light chain is identical to the corresponding residue in the donor antibody light chain.

In a sixteenth aspect, this invention provides a humanised anti-interleukin-18 antibody comprising:

(a) a heavy chain comprising CDRs derived from a donor antibody which CDRs have sequences set forth in SEQ ID NOs: 1, 2, and 3 grafted onto a human heavy chain acceptor framework which heavy chain acceptor framework comprises framework regions derived from the sequence set forth in SEQ ID NO: 37, wherein the residues at positions 27, 28, 29, 93 of the heavy chain are identical to the corresponding residues in the donor antibody heavy chain; and (b) a light chain comprising CDRs derived from a donor antibody which CDRs have sequences set forth in SEQ ID NO:4, 5, and 6 grafted onto a light chain acceptor framework which light chain acceptor framework comprises framework regions derived from the sequence set forth in SEQ ID NO:38, wherein residue at position 71 of the light chain of said anti-interleukin-18 antibody is identical to the corresponding residues in the donor antibody light chain.

In a seventeenth aspect, this invention provides a humanised anti-interleukin-18 antibody comprising:

(a) a heavy chain comprising CDRs derived from a donor antibody which CDRs have sequences set forth in SEQ ID NOs: 1, 2, and 3 grafted onto a human heavy chain acceptor framework, wherein said heavy chain acceptor framework comprises framework regions derived from the sequence set forth in SEQ ID NO: 37, wherein the residues at positions 27, 28, 29, 39, 40, and 93 of the heavy chain are identical to the corresponding residues in the donor antibody heavy chain; and (b) a light chain comprising CDRs derived from a donor antibody which CDRs have sequences set forth in SEQ ID NOs: 4, 5, and 6 grafted onto a light chain acceptor framework, wherein said light chain acceptor framework comprises framework regions derived from the sequence set forth in SEQ ID NO: 38, wherein the residue at position 71 of the light chain is identical to the corresponding residues in the donor antibody light chain.

In an eighteenth aspect, this invention provides a humanised anti-interleukin-18 antibody comprising:

(a) a heavy chain comprising CDRs derived from a donor antibody which CDRs have sequences set forth in SEQ ID NO: 1, 2, and 3 grafted onto a human heavy chain acceptor framework, wherein said heavy chain acceptor framework comprises framework regions derived from the sequence set forth in SEQ ID NO: 37, wherein residues at positions 27, 28, 29, 36, 39, 40, 71, 89, 91, and 93 of the heavy chain are identical to the corresponding residues in the donor antibody heavy chain; and (b) a light chain comprising CDRs derived from a donor antibody which CDRs have sequences set forth in SEQ ID NOs: 4, 5, and 6 grafted onto a light chain acceptor framework, wherein said light chain acceptor framework comprises framework regions derived from the sequence set forth in SEQ ID NO: 38, wherein the residue at position 71 of the light chain is identical to the corresponding residues in the donor antibody light chain.

In a nineteenth aspect, this invention provides a humanised anti-interleukin-18 antibody comprising:

(a) a heavy chain comprising CDRs derived from a donor antibody which CDRs have sequences set forth in SEQ ID NO: 1, 2, and 3 grafted onto a human heavy chain acceptor framework, wherein said heavy chain acceptor framework comprises framework regions derived from the sequence set forth in SEQ ID NO:37, wherein the residues at positions 27, 28, 29, and 93 of the heavy chain are identical to the corresponding residues in the donor antibody heavy chain; and (b) a light chain comprising CDRs derived from a donor antibody which CDRs have sequences set forth in SEQ ID NOs: 4, 5, and 6 grafted onto a light chain acceptor framework, wherein said light chain acceptor framework comprises framework regions derived from the sequence set forth in SEQ ID NO: 38, wherein the residues at positions 71, 45, 83, 84, and 85 of the light chain are identical to the corresponding residues in the donor antibody light chain.

In a twentieth aspect, this invention provides a humanised anti-interleukin-18 antibody comprising:

(a) a heavy chain comprising CDRs derived from a donor antibody which CDRs have sequences set forth in SEQ ID NOs: 1, 2, and 3 grafted onto a human heavy chain acceptor framework, wherein said heavy chain acceptor framework comprises framework regions derived from the sequence set forth in SEQ ID NO: 37, wherein the residues at positions 27, 28, 29, 93, 39, and 40 of the heavy chain are identical to the corresponding residues in the donor antibody heavy chain; and (b) a light chain comprising CDRs derived from a donor antibody which CDRs have sequences set forth in SEQ ID NOs: 4, 5, and 6 grafted onto a light chain acceptor framework, wherein said light chain acceptor framework comprises framework regions derived from the sequence set forth in SEQ ID NO: 38, wherein the residues at positions 71, 45, 83, 84, and 85 of the light chain are identical to the corresponding residues in the donor antibody light chain.

In twenty-first aspect, this invention provides a humanised anti-interleukin-18 antibody comprising:

(a) a heavy chain comprising CDRs derived from a donor antibody which CDRs have sequences set forth in SEQ ID NOs: 1, 2, and 3 grafted onto a human heavy chain acceptor framework, wherein said heavy chain acceptor framework comprises framework regions derived from the sequence set forth in SEQ ID NO: 37, wherein the residues at positions 27, 28, 29, 93, 39, 40, 36, 71, 89, and 91 of the heavy chain are identical to the corresponding residues in the donor antibody heavy chain; and (b) a light chain comprising CDRs derived from a donor antibody which CDRs have sequences set forth in SEQ ID NO: 4, 5, and 6 grafted onto a light chain acceptor framework which light chain acceptor framework comprises framework regions derived from the sequence set forth in SEQ ID NO: 38, wherein the residues at positions 71, 45, 83, 84, and 85 of the light chain are identical to the corresponding residues in the donor antibody light chain.

In a twenty-second aspect, this invention provides a humanised anti-interleukin-18 antibody comprising a heavy chain and a light chain, wherein a ratio between off-rate (kd) of said antibody from binding to human IL-18 at 25° C. to off-rate (kd) of said antibody from binding to human IL-18 at 37° C. is 1:5 or less, and wherein said antibody comprises CDRs derived from a donor antibody and a human acceptor framework, and wherein a residue at position 71 of the light chain of the human acceptor framework is substituted by the corresponding residue from the donor antibody. In one embodiment of this invention, the off-rate is measured using a Biacore™ T100 instrument and the conditions as set out in Example 4.b. below.

In a twenty-third aspect, this invention provides a humanised anti-interleukin-18 antibody comprising a heavy chain selected from the group consisting of: SEQ ID NO: 9, SEQ ID NO: 17, and SEQ ID NO: 21; and a light chain selected from the group consisting of: SEQ ID NO: 13 and SEQ ID NO: 29.

In particular, this invention provides a humanised anti-interleukin-18 antibody comprising a heavy chain of SEQ ID NO: 9 and a light chain of SEQ ID NO: 13, or a heavy chain of SEQ ID NO: 9 and a light chain of SEQ ID NO: 29.

This invention also provides a humanised anti-interleukin-18 antibody comprising a heavy chain of SEQ ID NO: 17 and a light chain of SEQ ID NO: 13, or a heavy chain of SEQ ID NO: 17 and a light chain of SEQ ID NO: 29.

This invention also provides a humanised anti-interleukin-18 antibody comprising a heavy chain of SEQ ID NO: 21 and a light chain of SEQ ID NO: 13 or a heavy chain of SEQ ID NO: 21 and a light chain of SEQ ID NO: 29.

In a twenty-fourth aspect, this invention provides a pharmaceutical composition comprising an anti-interleukin-18 antibody, as hereinbefore described, in combination with a carrier.

In a twenty-fifth aspect, this invention provides a method of selecting an antibody, particularly an antibody that inhibits the interaction between a ligand and a receptor, such as an anti-interleukin-18 antibody, for therapeutic use, wherein said method comprises the steps of:

(a) measuring the binding affinity (using, e.g., surface plasmon resonance, such as Biacore™) of the antibody for an antigen to which the antibody specifically binds at a temperature between 30 to 45° C. (preferably 37° C.);

(b) measuring the binding affinity (using, e.g., surface plasmon resonance, such as Biacore™) of the antibody for an antigen to which the antibody specifically binds at a temperature between 20 to 25° C. (preferably 25° C.); and (c) selecting said antibody for therapeutic use if the affinity of (a) is greater than the affinity of (b), preferably if said affinity of (a) is 2 fold or greater, more preferably 4 fold, or greater than the affinity of step (b).

In a twenty-sixth aspect, this invention provides a method of selecting an antibody, particularly an antibody that inhibits the interaction between a ligand and a receptor, such as an anti-interleukin-18 antibody, for therapeutic use, said method comprising the steps of:

(a) measuring the off-rate (using, e.g., surface plasmon resonance, such as Biacore™) of the antibody from the antigen to which the antibody specifically binds, at a temperature between 30 to 45° C. (preferably 37° C.);

(b) measuring the off-rate (using, e.g., surface plasmon resonance, such as Biacore™) of the antibody from the antigen to which the antibody specifically binds at a temperature between 20 to 25° C. (preferably 25° C.); and (c) selecting said antibody for therapeutic use if the off-rate of (a) is slower than the off-rate of (b).

The term "anti-interleukin-18" as it refers to antibodies of the invention means that such antibodies are capable of neutralising the biological activity of human interleukin-18. It does not exclude, however, that such antibodies may also in addition neutralise the biological activity of non-human primate (e.g., rhesus and/or cynomoglus) interleukin-18.

DETAILED DESCRIPTION OF THE INVENTION

The use of intact non-human antibodies in the treatment of human diseases or disorders carries with it the now well established problems of potential immunogenicity, especially upon repeated administration of the antibody. That is, the immune system of the patient may recognise the non-human intact antibody as non-self and mount a neutralising response. In addition to developing fully human antibodies (see above) various techniques have been developed over the years to overcome these problems and generally involve reducing the composition of non-human amino acid sequences in the intact therapeutic antibody whilst retaining the relative ease in obtaining non-human antibodies from an immunised animal, e.g., mouse, rat or rabbit. Broadly two approaches have been used to achieve this. The first are chimaeric antibodies, which generally comprise a non-human (e.g., rodent, such as mouse) variable domain fused to a human constant region, see Morrison (1984), PNAS, 81, 6851. Because the antigen-binding site of an antibody is localised within the variable regions the chimaeric antibody retains its binding affinity for the antigen but acquires the effector functions of the human constant region and is therefore able to perform effector functions such as described supra. Chimaeric antibodies are typically produced using recombinant DNA methods. DNA encoding the antibodies (e.g., cDNA) is isolated and sequenced using conventional procedures (e.g., by using oligonucleotide probes that are capable of binding specifically to genes encoding the H and L chains of the antibody of the invention, e.g., DNA encoding SEQ ID NOs: 1, 2, 3, 4, 5, and 6 described supra). Hybridoma cells serve as a typical source of such DNA. If it is desired to express the chimaeric antibody, isolated cDNAs encoding the entire mature variable regions of the light and heavy chains are inserted in-frame into suitable expression vectors which contain, inter alia, appropriate immunoglobulin constant regions, usually of human origin, together with signal sequences, stop codons, promoters, terminators and other elements as needed to obtain expression of the antibody. Such vectors are then transfected into host cells such as *E. Coli*, COS cells, CHO cells or myeloma cells that do not otherwise produce immunoglobulin protein to obtain synthesis of the antibody. The DNA may be modified by substituting the coding sequence for human L and H chains for the corresponding non-human (e.g., murine) H and L constant regions. See, e.g., Morrison; PNAS 81: 6851 (1984).

The second approach involves the generation of humanised antibodies, wherein the non-human content of the antibody is reduced by humanizing the variable regions. Two techniques for humanisation have gained popularity. The first is humanisation by CDR grafting. CDRs build loops close to the antibody's N-terminus where they form a surface mounted in a scaffold provided by the framework regions. Antigen-binding specificity of the antibody is mainly defined by the topography and by the chemical characteristics of its CDR surface. These features are, in turn, determined by the conformation of the individual CDRs, by the relative disposition of the CDRs, and by the nature and disposition of the side chains of the residues comprising the CDRs. A large decrease in immunogenicity can be achieved by grafting only the CDRs of a non-human (e.g. murine) antibodies ("donor" antibodies) onto a suitable human framework ("acceptor framework") and constant regions (see Jones, et al., (1986) *Nature* 321, 522-525 and Verhoeyen M, et al. (1988) *Science* 239, 1534-1536). However, CDR grafting per se may not result in the complete retention of antigen-binding properties and it is frequently found that some framework residues of the donor antibody need to be preserved (sometimes referred to as "backmutations") in the humanised molecule if significant antigen-binding affinity is to be recovered (see Queen C., et al., (1989) *PNAS* 86, 10,029-10,033, Co, M., et al., (1991) *Nature* 351, 501-502). In this case, human V regions showing the greatest sequence homology (typically 60% or greater) to the non-human donor antibody maybe chosen from a database in order to provide the human framework (FR). The selection of human FRs can be made either from human consensus or individual human antibodies. Where necessary key residues from the donor antibody are substituted into the human acceptor framework to preserve CDR conformations. Computer modelling of the antibody may be used to help identify such structurally important residues, see WO99/48523.

Alternatively, humanisation maybe achieved by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan E. A., et al., (1991) *Mol. Immunol.* 28, 489-498 and Pedersen J. T., et al., (1994) *J. Mol. Biol.* 235; 959-973). Therefore, it is possible to reduce the immunogenicity of a non-human Fv by replacing exposed residues in its framework regions that differ from those usually found in human antibodies. Because protein antigenicity can be correlated with surface accessibility, replacement of the surface residues may be sufficient to render the mouse variable region "invisible" to the human immune system (see also Mark G. E., et al., (1994) in *Handbook of Experimental Pharmacology vol.* 113: The pharmacology of monoclonal Antibodies, Springer-Verlag, pp 105-134). This procedure of humanisation is referred to as "veneering" because only the surface of the antibody is altered, the supporting residues remain undisturbed. Further alternative approaches include that set out in WO04/006955 and the process of Humaneering™ (Kalobios), which makes use of bacterial expression systems and priduces antibodies that are close to human germline in sequence (Alfenito-M Advancing Protein Therapeutics, January 2007, San Diego, Calif.). Another, recent approach to humanisation involves selecting human acceptor frameworks on the basis of structural similarity of the human CDR regions to those of the donor mouse antibody CDR regions rather than on homology between other regions of the antibody such as framework regions. This process is also known as Superhumanisation™ (Evogenix Inc.; Hwang, et al., (2005) *Methods* 36:35-42).

Thus, the present invention concerns humanised antibodies, as discussed above. In one embodiment of this invention, such humanised antibodies comprise a human constant region of an IgG isotype, such as IgG1 or IgG4. In alternative embodiments, the humanised variable regions, discussed above, that may be fused with a non-human constant region ("reverse chimera"), such as non-human primate, rat, murine or rabbit.

It will be apparent to those skilled in the art that the acceptor frameworks set forth in SEQ ID NO: 37 and 38 constitute immunoglobulin amino acids encoded by a VH and Vkappa gene, respectively. As such they comprise both the framework regions and the CDRs of the acceptor antibody. It is well within the capacity of the skilled person to substitute the acceptor antibody CDRs with the donor CDRs set forth in SEQ ID NOs: 1, 2, 3, 4, 5, and 6 and to associate the resulting sequences with suitable framework 4 sequences, such as those set forth in SEQ ID NO: 39 and SEQ ID NO: 40, so as to produce a complete immunoglobulin variable region such as set forth in SEQ ID NO: 11 and SEQ ID NO: 15.

The interaction between the Fc region of an antibody and various Fc receptors (FcγR) is believed to mediate the effector functions of the antibody which include antibody-dependent cellular cytotoxicity (ADCC), fixation of complement, phagocytosis and half-life/clearance of the antibody. Various modifications to the Fc region of antibodies of the invention may be carried out depending on the desired effector property. For example, specific mutations in the Fc region to render an otherwise lytic antibody, non-lytic is detailed in EP 0 629 240 B1 and EP 0 307 434 B2 or one may incorporate a salvage receptor binding epitope into the antibody to increase serum half life see U.S. Pat. No. 5,739,277. There are five currently recognised human Fcγ receptors, FcγR (I), FcγRIIa, FcγRIIb, FcγRIIIa and neonatal FcRn. Shields, et al., (2001) J. Biol. Chem 276, 6591-6604 demonstrated that a common set of IgG1 residues is involved in binding all FcγRs, while FcγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgG1 residues for binding, FcγRII and FcγRIII interact with distinct residues in addition to the common set. Alteration of some residues reduced binding only to FcγRII (e.g., Arg-292) or FcγRIII (e.g. Glu-293). Some variants showed improved binding to FcγRII or FcγRIII but did not affect binding to the other receptor (e.g., Ser-267Ala improved binding to FcγRII but binding to FcγRIII was unaffected). Other variants exhibited improved binding to FcγRII or FcγRIII with reduction in binding to the other receptor (e.g., Ser-298Ala improved binding to FcγRIII and reduced binding to FcγRII). For FcγRIIIa, the best binding IgG1 variants had combined alanine substitutions at Ser-298, Glu-333 and Lys-334. The neonatal FcRn receptor is believed to be involved in both antibody clearance and the transcytosis across tissues (see Junghans R. P (1997) Immunol. Res 16. 29-57 and Ghetie, et al., (2000) Annu. Rev. Immunol. 18, 739-766). Human IgG1 residues determined to interact directly with human FcRn includes Ile253, Ser254, Lys288, Thr307, Gln311, Asn434 and His435. The present invention therefore concerns antibodies of the invention having any one (or more) of the residue changes detailed above to modify half-life/clearance and/or effector functions such as ADCC and/or complement lysis.

Other modifications include glycosylation variants of the antibodies of the invention. Glycosylation of antibodies at conserved positions in their constant regions is known to have a profound effect on antibody function, particularly effector functioning such as those described above, see for example, Boyd, et al., (1996), Mol. Immunol. 32, 1311-1318. Glycosylation variants of the therapeutic antibodies or antigen binding fragments thereof of the present invention wherein one or more carbohydrate moiety is added, substituted, deleted or modified are contemplated. Introduction of an asparagine-X-serine or asparagine-X-threonine motif creates a potential site for enzymatic attachment of carbohydrate moieties and may therefore be used to manipulate the glycosylation of an antibody. In Raju, et al., (2001) Biochemistry 40, 8868-8876 the terminal sialyation of a TNFR-IgG immunoadhesin was increased through a process of regalactosylation and/or resialylation using beta-1, 4-galactosyltransferace and/or alpha, 2,3 sialyltransferase. Increasing the terminal sialylation is believed to increase the half-life of the immunoglobulin. Antibodies, in common with most glycoproteins, are typically produced in nature as a mixture of glycoforms. This mixture is particularly apparent when antibodies are produced in eukaryotic, particularly mammalian cells. A variety of methods have been developed to manufacture defined glycoforms, see Zhang, et al., Science (2004), 303, 371, Sears, et al., Science, (2001) 291, 2344, Wacker, et al., (2002) Science, 298 1790, Davis, et al., (2002) Chem. Rev. 102, 579, Hang, et al., (2001) Acc. Chem. Res 34, 727. Thus the invention concerns a plurality of therapeutic (typically monoclonal) antibodies (which maybe of the IgG isotype, e.g., IgG1) as described herein comprising a defined number (e.g., 7 or less, for example 5 or less such as two or a single) glycoform(s) of said antibodies or antigen binding fragments thereof.

Further embodiments of the invention include therapeutic antibodies of the invention or antigen binding fragments thereof coupled to a non-proteinaeous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments, see Koumenis I. L., et al., (2000) Int. J. Pharmaceut. 198:83-95.

Antibodies of the present invention may be produced in transgenic organisms such as goats (see Pollock, et al., (1999), J. Immunol. Methods 231:147-157), chickens (see Morrow K J J (2000) Genet. Eng. News 20:1-55), mice (see Pollock, et al., ibid) or plants (see Doran P M, (2000) Curr. Opinion Biotechnol. 11, 199-204, Ma JK-C (1998), Nat. Med. 4; 601-606, Baez J., et al., BioPharm (2000) 13: 50-54, Stoger E., et al., (2000) Plant Mol. Biol. 42:583-590). Antibodies may also be produced by chemical synthesis. However, antibodies of the invention are typically produced using recombinant cell culturing technology well known to those skilled in the art. A polynucleotide encoding the antibody is isolated and inserted into a replicable vector such as a plasmid for further cloning (amplification) or expression in a host cell. One useful expression system is a glutamate synthetase system (such as sold by Lonza Biologics), particularly where the host cell is CHO or NS0 (see below). Polynucleotide encoding the antibody is readily isolated and sequenced using conventional procedures (e.g., oligonucleotide probes). Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotide encoding the light and heavy chains may be inserted into separate vectors and introduced (e.g., by transformation, transfection, electroporation or transduction) into the same host cell concurrently or sequentially or, if desired both the heavy chain and light chain can be inserted into the same vector prior to such introduction.

It will be immediately apparent to those skilled in the art that due to the redundancy of the genetic code, alternative polynucleotides to those disclosed herein are also available that will encode the polypeptides of the invention.

Antibodies of the present invention maybe produced as a fusion protein with a heterologous signal sequence having a specific cleavage site at the N-terminus of the mature protein. The signal sequence should be recognised and processed by the host cell. For prokaryotic host cells, the signal sequence may be an alkaline phosphatase, penicillinase, or heat stable enterotoxin II leaders. For yeast secretion the signal sequences may be a yeast invertase leader, α factor leader or acid phosphatase leaders. See, e.g., WO90/13646. In mammalian cell systems, viral secretory leaders such as herpes simplex gD signal and a native immunoglobulin signal sequence (such as human Ig heavy chain) are available. Typically, the signal sequence is ligated in reading frame to polynucleotide encoding the antibody of the invention.

Origin of replications are well known in the art with pBR322 suitable for most gram-negative bacteria, 2μ plasmid for most yeast and various viral origins such as SV40, polyoma, adenovirus, VSV or BPV for most mammalian cells. Generally the origin of replication component is not needed for integrated mammalian expression vectors, unless vector propagation is required in $E.$ $coli$. However, the SV40 ori may be used since it contains the early promoter.

Typical selection genes encode proteins that (a) confer resistance to antibiotics or other toxins, e.g., ampicillin, neomycin, methotrexate or tetracycline or (b) complement auxotrophic deficiencies or supply nutrients not available in the complex media or (c) combinations of both. The selection scheme may involve arresting growth of the host cells that contain no vector or vectors. Cells, which have been successfully transformed with the genes encoding the therapeutic antibody of the present invention, survive due to, e.g., drug resistance conferred by the co-delivered selection marker. One example is the DHFR-selection system wherein transformants are generated in DHFR negative host strains (e.g., see Page and Sydenham 1991 *Biotechnology* 9: 64-68). In this system the DHFR gene is co-delivered with antibody polynucleotide sequences of the invention and DHFR positive cells then selected by nucleoside withdrawal. If required, the DHFR inhibitor methotrexate is also employed to select for transformants with DHFR gene amplification. By operably linking DHFR gene to the antibody coding sequences of the invention or functional derivatives thereof, DHFR gene amplification results in concomitant amplification of the desired antibody sequences of interest. CHO cells are a particularly useful cell line for this DHFR/methotrexate selection and methods of amplifying and selecting host cells using the DHFR system are well established in the art see Kaufman R. J., et al., J. Mol. Biol. (1982) 159, 601-621, for review, see Werner R G, Noe W, Kopp K, Schluter M, "Appropriate mammalian expression systems for biopharmaceuticals", Arzneimittel-Forschung. 48(8):870-80, 1998 August. A further example is the glutamate synthetase expression system (Lonza Biologics). A suitable selection gene for use in yeast is the trp1 gene; see Stinchcomb, et al., Nature 282, 38, 1979.

Suitable promoters for expressing antibodies of the invention are operably linked to DNA/polynucleotide encoding the antibody. Promoters for prokaryotic hosts include phoA promoter, Beta-lactamase and lactose promoter systems, alkaline phosphatase, tryptophan and hybrid promoters such as Tac. Promoters suitable for expression in yeast cells include 3-phosphoglycerate kinase or other glycolytic enzymes, e.g., enolase, glyceralderhyde 3 phosphate dehydrogenase, hexokinase, pyruvate decarboxylase, phosphofructokinase, glucose 6 phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include RNA polymerase II promoters including viral promoters such as polyoma, fowlpox and adenoviruses (e.g., adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40 and non-viral promoters such as EF-1alpha (Mizushima and Nagata Nucleic Acids Res 1990 18(17):5322. The choice of promoter may be based upon suitable compatibility with the host cell used for expression.

Where appropriate, e.g., for expression in higher eukaroytics, additional enhancer elements can be included instead of, or as well as, those found located in the promoters described above. Suitable mammalian enhancer sequences include enhancer elements from globin, elastase, albumin, fetoprotein, metallothionine and insulin. Alternatively, one may use an enhancer element from a eukaroytic cell virus such as SV40 enhancer, cytomegalovirus early promoter enhancer, polyoma enhancer, baculoviral enhancer or murine IgG2a locus (see WO04/009823). Whilst such enhancers are typically located on the vector at a site upstream to the promoter, they can also be located elsewhere, e.g., within the untranslated region or downstream of the polydenalytion signal. The choice and positioning of enhancer may be based upon suitable compatibility with the host cell used for expression.

In eukaryotic systems, polyadenylation signals are operably linked to polynucleotide encoding the antibody of this invention. Such signals are typically placed 3' of the open reading frame. In mammalian systems, non-limiting example signals include those derived from growth hormones, elongation factor-1 alpha and viral (eg SV40) genes or retroviral long terminal repeats. In yeast systems non-limiting examples of polydenylation/termination signals include those derived from the phosphoglycerate kinase (PGK) and the alcohol dehydrogenase 1 (ADH) genes. In prokaryotic system polyadenylation signals are typically not required and it is instead usual to employ shorter and more defined terminator sequences. The choice of polyadenylation/termination sequences may be based upon suitable compatibility with the host cell used for expression.

In addition to the above, other features that can be employed to enhance yields include chromatin remodelling elements, introns and host-cell specific codon modification. The codon usage of the antibody of this invention thereof can be modified to accommodate codon bias of the host cell such to augment transcript and/or product yield (eg Hoekema A., et al., Mol Cell Biol 1987 7(8):2914-24). The choice of codons may be based upon suitable compatibility with the host cell used for expression.

Suitable host cells for cloning or expressing vectors encoding antibodies of the invention are prokaroytic, yeast or higher eukaryotic cells. Suitable prokaryotic cells include eubacteria, e.g., enterobacteriaceae such as *Escherichia* e.g. *E. Coli* (for example ATCC 31, 446; 31, 537; 27, 325), *Enterobacter, Erwinia, Klebsiella Proteus, Salmonella*, e.g., *Salmonella typhimurium, Serratia*, e.g., *Serratia marcescans* and *Shigella* as well as *Bacilli* such as *B. subtilis* and *B. licheniformis* (see DD 266 710), *Pseudomonas* such as *P. aeruginosa* and *Streptomyces*. Of the yeast host cells, *Saccharomyces cerevisiae, Schizosaccharomyces pombe, Kluyveromyces* (e.g., ATCC 16,045; 12,424; 24178; 56,500), *yarrowia* (EP402, 226), *Pichia Pastoris* (EP183, 070, see also Peng, et al., J. Biotechnol. 108 (2004) 185-192), *Can-* dida, *Trichoderma reesia* (EP244, 234), Penicillin, *Tolypocladium* and *Aspergillus* hosts such as *A. nidulans* and *A. niger* are also contemplated.

Although Prokaryotic and yeast host cells are specifically contemplated by the invention, typically however, host cells of the present invention are vertebrate cells. Suitable vertebrate host cells include mammalian cells such as COS-1 (ATCC No. CRL 1650) COS-7 (ATCC CRL 1651), human embryonic kidney line 293, PerC6 (Crucell), baby hamster kidney cells (BHK) (ATCC CRL. 1632), BHK570 (ATCC NO: CRL 10314), 293 (ATCC NO. CRL 1573), Chinese hamster ovary cells CHO (e.g., CHO-K1, ATCC NO: CCL 61, DHFR-CHO cell line such as DG44 (see Urlaub, et al., (1986) ibid), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells, e.g., NS0 (see U.S. Pat. No. 5,807,715), Sp2/0, Y0.

Thus, one embodiment of this invention provides a stably transformed host cell comprising a vector encoding a heavy chain and/or light chain of the therapeutic antibody as described herein. Typically, such host cells comprise a first vector encoding the light chain and a second vector encoding said heavy chain. Such host cells may also be further engineered or adapted to modify quality, function and/or yield of the antibody of this invention. Non-limiting examples include expression of specific modifying (eg glycosylation) enzymes and protein folding chaperones.

Host cells transformed with vectors encoding the therapeutic antibodies of the invention may be cultured by any method known to those skilled in the art. Host cells may be cultured in spinner flasks, shake flasks, roller bottles or hollow fibre systems but it is preferred for large scale production that stirred tank reactors or bag reactors (e.g., Wave Biotech, Somerset, N.J. USA) are used particularly for suspension cultures. Typically the stirred tankers are adapted for aeration using, e.g., spargers, baffles or low shear impellers. For bubble columns and airlift reactors direct aeration with air or oxygen bubbles maybe used. Where the host cells are cultured in a serum free culture media it is preferred that the media is supplemented with a cell protective agent such as pluronic F-68 to help prevent cell damage as a result of the aeration process. Depending on the host cell characteristics, either microcarriers maybe used as growth substrates for anchorage dependent cell lines or the cells maybe adapted to suspension culture. The culturing of host cells, particularly vertebrate host cells may utilise a variety of operational modes such as batch, fed-batch, repeated batch processing (see Drapeau, et al., (1994) *Cytotechnology* 15: 103-109), extended batch process or perfusion culture. Although recombinantly transformed mammalian host cells may be cultured in serum-containing media such media comprising fetal calf serum (FCS), it is preferred that such host cells are cultured in synthetic serum-free media such as disclosed in Keen, et al., (1995) *Cytotechnology* 17:153-163, or commercially available media such as ProCHO-CDM or UltraCHO™ (Cambrex N J, USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see, e.g., Scharfenberg K., et al., (1995) in *Animal Cell technology: Developments towards the 21st century* (Beuvery E. C., et al., eds), pp 619-623, Kluwer Academic publishers).

Antibodies of the invention secreted into the media may be recovered and purified from the media using a variety of techniques to provide a degree of purification suitable for the intended use. For example the use of therapeutic antibodies of the invention for the treatment of human patients typically mandates at least 95% purity as determined by reducing SDS-PAGE, more typically 98% or 99% purity, when compared to the culture media comprising the therapeutic antibodies. In the first instance, cell debris from the culture media is typically removed using centrifugation followed by a clarification step of the supernatant using, e.g., microfiltration, ultrafiltration and/or depth filtration. Alternatively, the antibody can be harvested by microfiltration, ultrafiltration or depth filtration without prior centrifugation. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. In one embodiment, the antibodies of the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g., nanofiltration using, e.g., a DV-20 filter). Following these various steps, a purified (typically monoclonal) preparation comprising at least 10 mg/ml or greater, e.g., 100 mg/ml or greater of the antibody of the invention is provided and therefore forms an embodiment of the invention. Concentration to 100 mg/ml or greater can be generated by ultracentrifugation. Suitably such preparations are substantially free of aggregated forms of antibodies of the invention.

Bacterial systems are particularly suited for the expression of antibody fragments. Such fragments are localised intracellularly or within the periplasma. Insoluble periplasmic proteins can be extracted and refolded to form active proteins according to methods known to those skilled in the art, see Sanchez, et al., (1999) *J. Biotechnol*. 72, 13-20 and Cupit P. M., et al., (1999) *Lett Appl Microbiol*, 29, 273-277.

Purified preparations of antibodies of the invention (particularly monoclonal preparations) as described supra, may be incorporated into pharmaceutical compositions for use in the treatment of human diseases and disorders such as those outlined above. Typically such compositions further comprise a pharmaceutically acceptable (i.e., inert) carrier as known and called for by acceptable pharmaceutical practice, see, e.g., Remingtons Pharmaceutical Sciences, 16th ed, (1980), Mack Publishing Co. Examples of such carriers include sterilised carrier such as saline, Ringers solution or dextrose solution, buffered with suitable buffers to a pH within a range of 5 to 8. Pharmaceutical compositions for injection (e.g., by intravenous, intraperitoneal, intradermal, subcutaneous, intramuscular or intraportal) or continuous infusion are suitably free of visible particulate matter and may comprise between 0.1 ng to 100 mg of antibody, typically between 5 mg and 25 mg of antibody. Methods for the preparation of such pharmaceutical compositions are well known to those skilled in the art. In one embodiment, pharmaceutical compositions comprise between 0.1 ng to 100 mg of therapeutic antibodies of the invention in unit dosage form, optionally together with instructions for use.

Pharmaceutical compositions of the invention may be lyophilised (freeze dried) for reconstitution prior to administration according to methods well known or apparent to those skilled in the art. Where embodiments of the invention comprise antibodies of the invention with an IgG1 isotype, a chelator of copper such as citrate (e.g., sodium citrate) or EDTA or histidine may be added to the pharmaceutical composition to reduce the degree of copper-mediated degradation of antibodies of this isotype. See EP 0 612 251.

Effective doses and treatment regimes for administering the antibody of the invention are generally determined empirically and are dependent on factors such as the age, weight and health status of the patient and disease or disorder to be treated. Such factors are within the purview of the attending physician. Guidance in selecting appropriate doses may be found in, e.g., Smith, et al., (1977) Antibodies in human diagnosis and therapy, Raven Press, New York but will in general be between 1 mg and 1000 mg. In one embodiment, the dosing regime for treating a human patient afflicted with RA is 100 mg or thereabout (i.e., between 50 mg to 200 mg) of antibody of the invention (or antigen binding fragment thereof) administered subcutaneously per week or every two weeks. Compositions of the present invention may also be used prophylactically.

Depending on the disease or disorder to be treated, pharmaceutical compositions comprising a therapeutically effective amount of the antibody of the invention may be used simultaneously, separately or sequentially with an effective amount of another medicament such as an anti-inflammatory agent for example a NSAID, methotrexate, bucillamine, sodium thiomalate or one or more of an anti-TNF alpha treatment such as Enbrel™ (etanercept), Remicade™ (infliximab), Humira™ (adalimumab) and/or CDP870. Antibodies of the invention maybe used in combination with an effective amount of an anti-TNF-alpha receptor antibody, see Davis M. W., et al., (2000) Ann Rheum Dis 59(Suppl 1): 41-43. In other embodiments, antibodies of the invention maybe used in combination with an effective amount of an agent directed against; IL-1/IL-1R (e.g., Kineret™), CTLA4-Ig, IL-6 (see Choy, et al., (2002) Ann. Rheum. Dis 61(suppl 1): 54), IL-8, IL-15, VEGF, IL-17, IL-18 (see Taylor, et al., (2001) Curr. Opin. Immunol. 13: 611-616), anti-ICAM and/or anti-CD4 antibodies, agents directed against a member of the MMP family, e.g., MMP-1, 2, 3 and/or 13. Antibodies of the invention may also be used in combination with an agent that ablates cells known to be involved in the inflammatory process, e.g., CD20 positive B cells using for example Mabthera™ (Rituximab). Other therapies in combination with antibodies of the invention include anti-angiogenic therapies such as antagonists of the integrin $\alpha_v\beta_3$, Kringles 1-5 (see Sumariwalla P., et al., (2003), *Arthritis Res Ther* 5:R32-R39.), soluble Flt-1 (see Miotla, et al., (2000) *Lab. Invest.* 80:1195-1205), an anti-COX-2 agent or an anti-OSM agent such as an anti-OSM antibody, see WO2005/095457, the entire contents of which are specifically incorporated herein by reference. Conveniently, a pharmaceutical composition comprising a kit of parts of the antibody of the invention or antigen binding fragment thereof together with such another medicaments optionally together with instructions for use is also contemplated by the present invention. These combinations maybe particularly useful in the treatment of arthritic diseases/disorders such as rheumatoid arthritis.

Antibodies of the invention may be used in therapeutic treatments of IL-18-mediated diseases such as autoimmune diseases. Particular mention is made of multiple sclerosis, arthritic diseases such as rheumatoid arthritis, Type 1 diabetes, inflammatory bowel disease (IBD) and psoriasis. Thus the invention further comprises a method of treating a human patient afflicted with a disease responsive to neutralisation of hIL-18 (such as multiple sclerosis, rheumatoid arthritis, Type 1 diabetes, IBD, psoriasis), which method comprises administering to said patient a therapeutically effective amount of an antibody of the invention, particularly an antibody having a heavy chain with a sequence set forth in SEQ ID NO: 9 and a light chain having the sequence set forth in SEQ ID NO: 13.

Use of an antibody of the invention in the manufacture of a medicament for the treatment of any one (or more) of the above mentioned diseases/disorders is also provided. Table A below gives a protein or polynucleotide description for each Sequence Identifier (SEQ ID NO:) used in this application.

TABLE A

| Protein or polynucleotide (PN) description | Sequence Identifier (SEQ ID NO:) |
|---|---|
| CDRH1 | 1 |
| CDRH2 | 2 |
| CDRH3 | 3 |
| CDRL1 | 4 |
| CDRL2 | 5 |
| CDRL3 | 6 |
| Human IL-18 | 7 |
| Human Il-18 PN | 8 |
| H1 heavy chain (variable + constant region) | 9 |
| H1 heavy chain (PN) | 10 |
| H1 variable region | 11 |
| H1 variable region (PN) | 12 |
| L2 light chain (variable + constant region) | 13 |
| L2 light chain (PN) | 14 |
| L2 variable region | 15 |
| L2 variable region (PN) | 16 |
| H2 heavy chain (variable + constant) | 17 |
| H2 heavy chain (PN) | 18 |
| H2 variable region | 19 |
| H2 variable region (PN) | 20 |
| H3 heavy chain (variable + constant) | 21 |
| H3 heavy chain (PN) | 22 |
| H3 variable region | 23 |
| H3 variable region (PN) | 24 |
| L1 light chain (variable and constant region) | 25 |
| L1 light chain (PN) | 26 |
| L1 variable region | 27 |
| L1 variable region (PN) | 28 |
| L3 light chain (variable + constant region) | 29 |
| L3 light chain (PN) | 30 |
| L3 variable region | 31 |
| L3 variable region (PN) | 32 |
| 2c10 rat-human IgG1 chimera | 33 |
| 2c10 rat-human IgG1 chimera (PN) | 34 |
| 2c10 rat-human CKappa chimera | 35 |
| 2c10 rat-human CKappa chimera (PN) | 36 |
| Heavy chain acceptor framework | 37 |
| Light chain acceptor framework | 38 |
| JH6 amino acid sequence added to SEQ ID NO: 37 | 39 |
| Jkappa 2 amino acid sequence added to SEQ ID NO: 38 | 40 |

BIOLOGICAL METHODS/EXAMPLES

The following examples illustrate various aspects of this invention. All general cloning, ligation and other recombinant DNA technology are performed as generally taught in Maniatis, et al., Molecular cloning (A laboratory manual), Cold Spring Harbor Laboratory, or Sambrook, et al., Molecular Cloning (A laboratory manual), Cold Spring Harbor Laboratory. Vector systems and additional molecular biology methods used herein are disclosed in WO2005/095457, the entire contents of which are incorporated herein by reference.

Example 1: Cloning of Hybridoma Variable Regions

The parental rat antibody 2C10 is set forth in U.S. Pat. No. 6,706,487. A chimaeric antibody 2C10c was designed based on the published rat V-regions described above joined to human IgG1 or kappa C-regions. A generic immunoglobulin signal sequence and translation start codon ATG was introduced for heavy and light chain constructs. Hind III and BsiWI restriction endonuclease sites were designed to frame the VL domain and allow cloning into mammalian expression vectors already containing the human Ckappa region (SEQ ID NO:36). Hind III and SpeI restriction endonuclease sites were designed to frame the VH domain and allow cloning into mammalian expression vectors already containing the human γ1 C-region (SEQ ID NO:34). This resulted in a two amino acid change for the 2C10 Vh region in framework 4 (Kabat residues 107 and 108) from the published sequence as shown in SEQ ID NO: 33.

Figure 15:
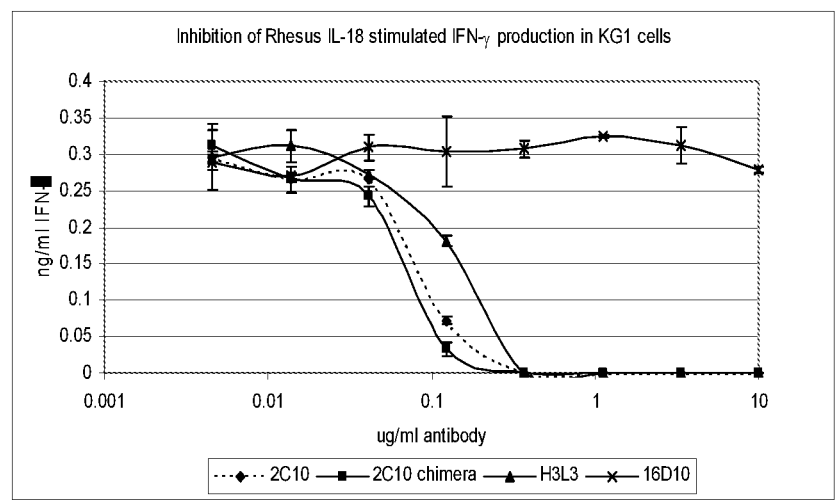
FIG. 15 shows inhibition of rhesus IL-18 stimulated IFN-γ production in KG1 cells.
Figure 16:
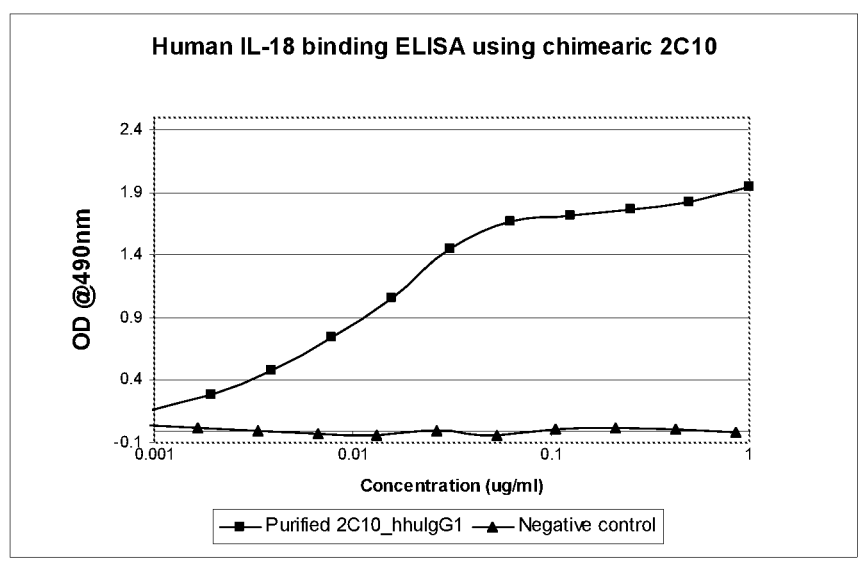
FIG. 16 shows the results of a human IL-18 binding ELISA using chimearic 2C10.
Figure 17:
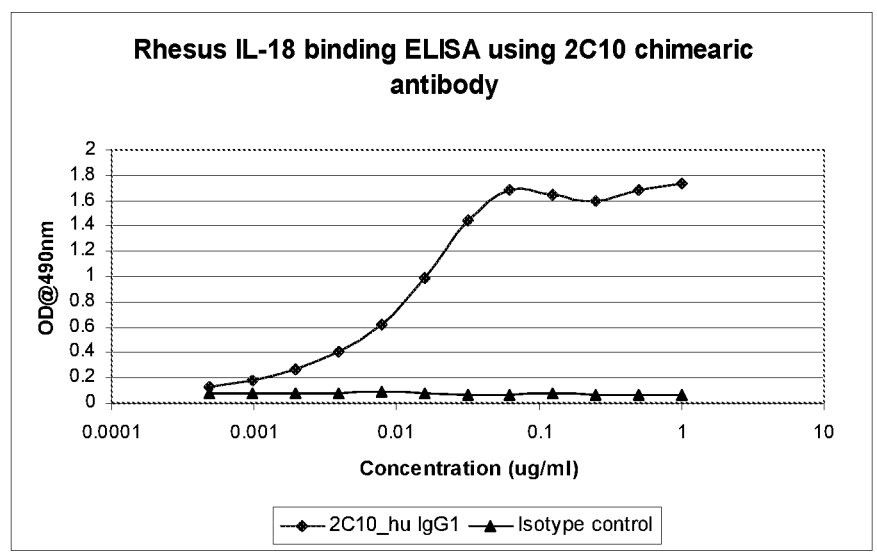
FIG. 17 shows the results of a rhesus IL-18 binding ELISA using chimearic 2C10.

Overlapping oligonucleotides were used to build the entire coding sequence by PCR and cloning into the expression vectors outlined above. After sequence verification, the chimaeric antibody was expressed CHO cells. Antibody produced was purified from cell culture supernatants by affinity chromatography on rProtein A Sepharose. Chimeric antibodies of 2C10 were evaluated in in vitro binding assays to demonstrate comparable potency to the parental rat 2C10. This was achieved by determining EC50 values for binding to human or rhesus IL-18 in ELISA (FIGS. 16 and 17) or by inhibition of IFN-γ release in KG-1 bioassay. See FIG. 15.

Example 2: Humanisation a. Light Chain Humanisation Strategy

For the 2C10 rat variable light chain sequence, a human germ line acceptor framework was selected (F_IGKV1D-12-1, SEQ ID NO:38), which had 64% identity (including CDRs), with the rat 2C10 variable light chain sequence. The germline V region was combined, in silico, with a suitable FR4, in this case the J-region kappa 2 minigene (Kabat Vol. II) based on sequence similarity (SEQ ID NO:40). Three humanised variants were generated on the basis of sequence comparison and possible impact on antibody function. Construct L1 was a straight graft of rat CDRs (using the Kabat definition) into the human acceptor framework selected above. Construct L2 was based on L1 with one additional back-mutation at residue 71. Construct L3 was based on L2 with 4 additional back-mutations at residues 45, 83, 84 and 85. See Table 1 below.

TABLE 1

Summary of humanised VL variants generated

| Construct | Acceptor/template Framework | Back-mutations@ aa# (Kabat) | Total number of back-mutations | Human acceptor framework | Original rat sequence |
|---|---|---|---|---|---|
| L1 | F_IGV1D-12-1/J2 (SEQ ID NO: 38) | ------ | NONE | ---- | ------ |
| L2 | L1 | 71 | 1 | F | Y |
| L3 | L2 | 45 | 5 | K | Q |
|  |  | 83 |  | F | E |
|  |  | 84 |  | A | G |
|  |  | 85 |  | T | D | b. Heavy Chain Humanisation Strategy

For the 2C10 rat variable heavy chain sequence a human germ line acceptor framework was selected (Fp_IGHV1-f_2, SEQ ID NO:37), which had 59% identity (including CDRs) with the rat 2C10 variable heavy chain. The germline V region was combined, in silico, with a suitable FR4, in this case, the JH6 minigene (Kabat Vol. II), based on sequence similarity (SEQ ID No:39). Three humanised variable heavy chain variants were designed based on this framework. H1 is a graft of the rat CDRs (using the Kabat definition with 4 additional back-mutations at residues 27, 28, 29 and 93. This allowed for a very unusual amino acid sequence just upstream to CDR1 of parental (i.e., donor) antibody that may constitute part of the CDR (as defined by Chothia). H2 was based on H1 with two additional back-mutations at residues 39 and 40. H3 was in turn based on H2 with another 4 additional back-mutations at residues 36, 71, 89 and 91. See Table 2 below.

TABLE 2

Summary of humanised Vh variants generated

| Construct | Acceptor/template Frameworks | Back-mutations @ aa# (Kabat) | Total number of back-mutations | Human acceptor framework | Original rat sequence |
|---|---|---|---|---|---|
| H1 | Fp_IGHV1-f_2 (SEQ ID NO: 37) | 27 | 4 | Y | E |
|  |  | 28 |  | T | I |
|  |  | 29 |  | L | S |
|  |  | 93 |  | A | T |
| H2 | H1 | 39 | 6 | Q | R |
|  |  | 40 |  | A | R |
| H3 | H2 | 36 | 10 | W | F |
|  |  | 71 |  | E | A |
|  |  | 89 |  | V | T |
|  |  | 91 |  | Y | F |

Example 3: Humanisation of 2C10C

Humanised V regions were synthesised de novo by build up of overlapping oligonucleotide and PCR amplification.

Primers included restriction sites for cloning into mammalian expression vectors and human immunoglobulin signal sequences for secretion. The humanised V regions were cloned into mammalian expression vectors as H1, H2 and H3 using HindIII and SpeI mammalian expression vectors containing the human gamma 1 constant region and as L1, L2 and L3 using HindIII and BsiWI into mammalian expression vectors containing the human kappa constant region. This generated humanised heavy chain variants of human IgG1 isotype and humanised light chain variants of human kappa isotype.

a. Expression of Humanised Heavy and Light Chain Antibody Combinations

CHOK1 cells were transiently transfected in quadruplicate. Supernatants were assayed for antibody concentration and then used in in vitro binding assays by comparing to 2C10 rat-human chimera.

Larger scale transient expression for all 9 variants was performed by mixing, for each flask, 51.4 µg of light chain plasmid and 8.6 ug of heavy chain plasmid with 240 µg of transfection lipid (this lipid is described in WO2006/053783, example 13, the entire contents of which are incorporated herein by reference) in 8 ml of medium (OptiMEM/glutamax/5% FBS) and applying this mixture to two near confluent T175 flask of CHOK1 cells for 72 hours under typical tissue culture conditions. Antibodies were also expressed in a polyclonal CHO cell system at mg quantity using shaker flasks and purified using FPLC and protein A.

Example 4: In Vitro Binding Assays a. Biacore™ Analysis

Biacore™ kinetic analysis of the humanised 2C10 antibodies was carried out on a Biacore™ 3000 instrument using Protein A capture of the antibodies in HBS-EP buffer (Biacore™). Briefly, Protein A was immobilised on a CM5 chip by primary amine coupling, using manufacturers recommended protocol, to densities around 2000-4000 resonance units (RU's). Humanised antibody was then passed over the Protein A surface and captured to levels of around 200-500 RU's, after a period of stabilisation, IL-18 (human or Rhesus) was passed over the captured antibody surface at defined concentrations and binding sensorgrams were obtained. Regeneration, using acidic elution conditions resulted in total removal of the captured antibody from the Protein A surface, and did not significantly reduce the surface's binding capacity. All curves were double referenced against a buffer injection instead of IL-18 and the data was fitted to the 1:1 binding model using the global fit parameters in BiaEval 4.1. Off-rate ranking experiments were set up using the same Protein A capture method, however, only a single concentration of IL-18 was used (10 nM). Whilst the data was fitted using the same binding model as the kinetic analysis, since only one concentration of analyte was used on the off-rate is reported, this value is useful for ranking rather than giving an exact kinetic measurement and was used as a way of selecting which antibodies would be further investigated.

Initial results at 25° C. indicated that all the constructs had similar binding affinities to human IL-18 as the rat 2C10 parental antibody. However when an off-rate ranking experiment was carried out at 37° C., the L1 constructs performed poorly compared to the L2, and L3 constructs with an increase seen in the off-rates (Table 3a and 3b).

TABLE 3a

Kinetic Parameters for Biacore Analysis of Human Anti-IL-18 Antibodies, Assayed at 25° C.

| ANTIBODY | Ka | Kd | KD (pM) |
|---|---|---|---|
| 2C10c | 2.55e6 (7e4) | 3.5e−5 (4.2e−6) | 13.9 (2.2) |
| H1L1 | 1.4e6 | 4.7e−5 | 33.2 |
| H1L2 | 1.3e6 (1.4e5) | 3.85e−5 (1.5e−5) | 30.3 (8.7) |
| H1L3 | 1.25e6 (2.1e4) | 2.8e−5 (5.7e−6) | 22.5 (7.2) |
| H2L1 | 1.03e6 (1.0e5) | 3.35e−5 (1.1e−5) | 33.5 (13.4) |
| H2L2 | 1.4e6 (1.4e5) | 2.8e−5 (0.0) | 20.1 (1.8) |
| H2L3 | 1.15e6 (7e5) | 2.8e−5 (2.8e−6) | 23.8 (0.7) |
| H3L1 | 2.5e6 (4.2e5) | 4.7e−5 (9.9e−6) | 19.4 (7.6) |
| H3L2 | 2.6e6 (2.8e5) | 4.3e−5 (3.6e−6) | 16.5 (2.7) |
| H3L3 | 1.7e6 (4.2e5) | 4.0e−5 (5.7e−6) | 24.2 (9.3) |

Data the result of two experiments, (standard deviation).

TABLE 3b

Off-Rate Ranking Biacore Analysis of Human IL-18 Binding to Protein A Captured Humanised Anti-IL-18 Antibodies, Assayed at 37° C.

| ANTIBODY | kd |
|---|---|
| 2C10c | 7.01E−5 |
| H1L1 | 1.62E−4 |
| H1L2 | 4.81e−5 |
| H1L3 | 5.54e−5 |
| H2L1 | 9.93E−5 |
| H2L2 | 4.15E−5 |
| H2L3 | 4.62E−5 |
| H3L1 | 1.3E−4 |
| H3L2 | 8.22E−5 |
| H3L3 | 7.01E−5 |

Data the result of one experiment

As well as performing poorly at 37° C., the L1 constructs were also worst in terms of affinity for binding to Rhesus IL-18 (Table 4a) at 25° C. Based upon these observations selected antibodies were investigated in greater detail for binding to human and Rhesus IL-18 at 37° C. The data shown in Table 4b for human IL-18 is the mean (and standard deviation) of six separate determinations. The data for Rhesus IL-18 shows the mean and standard deviation of two experiments for H1L2 and H1L3, whilst the data for H3L2 and H3L3 is from a single experiment. The comparatively high standard deviations of this data are probably a result of conducting this experiment at 37° C.

The fact that the L1 constructs performed relatively poorly is surprising when one considers that the difference between L1 and the L2 construct is the substitution of a phenylalanine by a tyrosine backmutation at position 71 of the light chain. Both tyrosine and phenylalanine are of course aromatic amino acids so the fact that such a subtle change in framework structure gave rise to marked results (in terms of binding affinity) observed in the Biacore™ system at 37° C. (but not 25° C.) was unexpected.

TABLE 4a

Kinetic Parameters for Biacore Analysis of Rhesus IL-18 Binding to Humanised Antibody Constructs Assayed at 25° C.

| ANTIBODY | Ka | Kd | KD (pM) |
|---|---|---|---|
| 2C10c | 1.2E6 | 6.6E−5 | 54.7 |
| H1L1 | 4.3E5 | 1.6E−4 | 380 |
| H1L2 | 4.3E5 | 4.7E−5 | 108 |
| H1L3 | 5.8E5 | 6.4E−5 | 109 |
| H2L1 | 2.9E5 | 1.8E−4 | 627 |

TABLE 4a-continued

Kinetic Parameters for Biacore Analysis of Rhesus IL-18
Binding to Humanised Antibody Constructs Assayed at 25° C.

| ANTIBODY | Ka | Kd | KD (pM) |
|---|---|---|---|
| H2L2 | 5.3E5 | 5.5E−5 | 104 |
| H3L1 | 9.1E5 | 1.4E−4 | 149 |
| H3L2 | 1.1E6 | 6.6E−5 | 59.6 |

Data the result of one experiment.

TABLE 4b

Kinetic Parameters for Biacore Analysis of Human and
Rhesus IL-18 Binding to Selected Humanised Antibody
Constructs Assayed at 37° C.

| Antibody/IL-18 | Ka | Kd | KD (pM) |
|---|---|---|---|
| H1L2 | | | |
| Human IL-18 | 7.75e5 (2.9e4) | 1.38e−4 (1.7e−5) | 197 (66.3) |
| Rhesus IL-18 | 1.01e6 (9.2e5) | 1.40e−4 (2.1e−5) | 139 (8.5) |
| H1L3 | | | |
| Human IL-18 | 7.12e5 (2.5e4) | 1.18e−4 (1.9e−5) | 188 (81) |
| Rhesus IL-18 | 1.08e6 (2.2e5) | 1.86e−4 (6.1e−5) | 170 (21.9) |
| H3L2 | | | |
| Human IL-18 | 1.52e6 (4.9e5) | 1.45e−4 (2.2e−5) | 105 (39.6) |
| Rhesus IL-18 | 1.85e6 | 1.19e−4 | 64.3 |
| H3L3 | | | |
| Human IL-18 | 1.49e6 (4.5e5) | 1.52e−4 (1.7e−5) | 110 (36.1) |
| Rhesus IL-18 | 1.79e6 | 1.35e−4 | 75.6 |

The variants H1L1, H1L2 and H1L3 were selected for further analysis in Example 4b below.

b. Biacore Analysis T100 Data

Characterisation of certain variant antibodies was further carried out using the T100 Biacore™ machine. This machine offers advantages over the Biacore™ 3000, in terms of sensitivity, temperature control and stability of baseline at higher temperatures due to the use of an inline degasser which minimises buffer effects at higher temperatures. It also offers enhanced software, such as automatic data analysis.

The methodology was basically the same as for the method used in Example 4a above; Protein A was immobilised on a CM5 chip at densities of between 2000-6000RU's by primary amine coupling. Runs were carried out in HBS-EP (Biacore™) The anti-IL-18 antibodies were captured to densities of between 100-500 RUs, human IL-18 was passed over this captured surface at concentrations between 16-0.0625 nM, with 0 nM concentration (i.e., a buffer only injection of captured antibody) used for double referencing. Regeneration after each injection of IL-18 was by mild acidic elution using two injections of 10 mM glycine, pH1.5. This regeneration step removed the captured antibody from the Protein A surface (and hence any IL-18 bound to it). The regeneration did not significantly alter the Protein A surfaces' ability to bind subsequent pulses of antibody, allowing another capture event to occur. The binding curves obtained were analysed using the analysis software inherent to the T100 machine using the 1:1 model of binding. Runs were carried out at the temperatures indicated.

c. Analysis of Binding of H1L1 and H1L2 at 15° C., 20° C., 25° C., 32° C. and 37° C.

Figure 2:
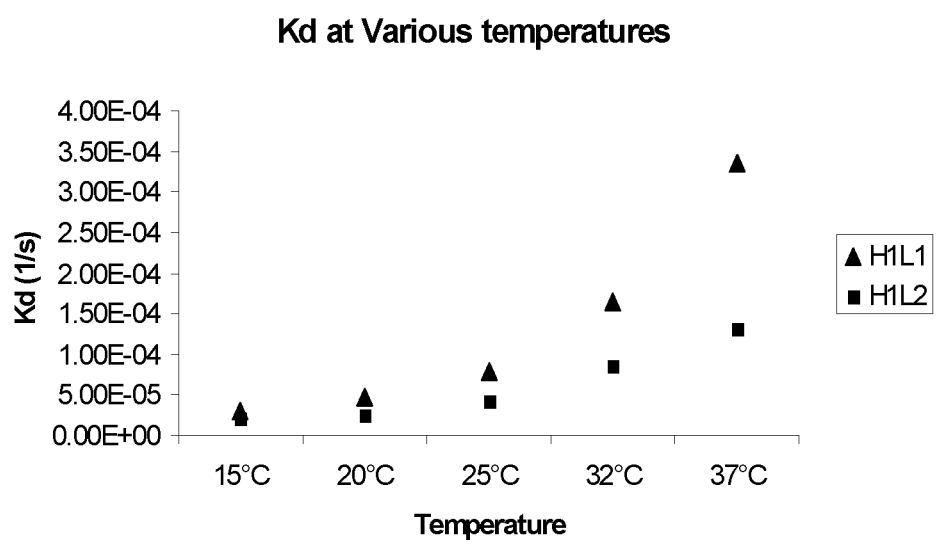
FIG. 2 shows the effect of temperature on the off-rate (kd).
Figure 3:
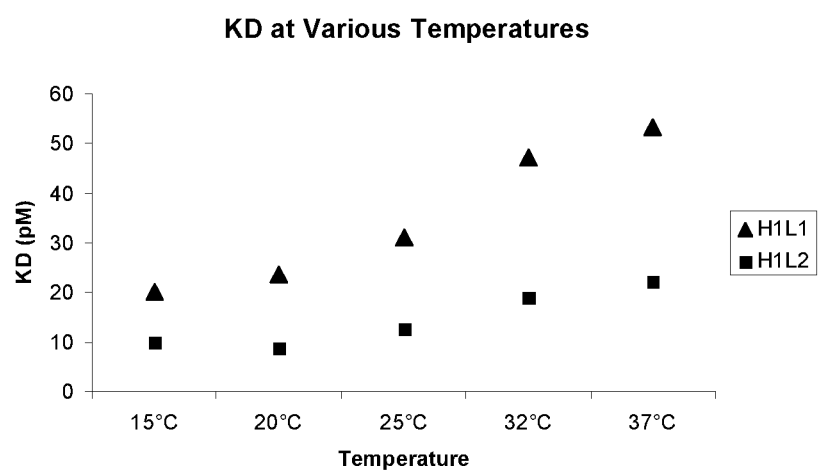
FIG. 3 shows the effect of temperature on the equilibrium constant (KD).

This experiment was carried out using the above method at various temperatures. FIG. 1 shows the effect of temperature on the on-rate (ka), while FIG. 2 shows the effect on off-rate (kd). FIG. 3 shows the effect on the equilibrium constant (KD). Table 5 details the kinetic values used to create these figures.

TABLE 5

Kinetic Parameters from the Temperature Variation Experiment

| Temp ° C. | Antibody | Ka | Kd | KD (pM) |
|---|---|---|---|---|
| 15 | H1L1 | 1.49e6 | 2.98e−5 | 20.1 |
|  | H1L2 | 2.07e6 | 2.07e−5 | 10.0 |
| 20 | H1L1 | 2.02e6 | 4.77e−5 | 23.7 |
|  | H1L2 | 2.84e6 | 2.53e−5 | 8.9 |
| 25 | H1L1 | 2.52e6 | 7.82e−5 | 31.1 |
|  | H1L2 | 3.37e6 | 4.22e−5 | 12.5 |
| 32 | H1L1 | 3.48e6 | 1.64e−4 | 47.2 |
|  | H1L2 | 4.51e6 | 8.57e−5 | 18.9 |
| 37 | H1L1 | 6.30e6 | 3.36e−4 | 53.3 |
|  | H1L2 | 5.89e6 | 1.31e−4 | 22.3 |

The data is from a single experiment.

The data shows that the on-rates of the two antibodies tested are similar over the temperature range tested, with H1L2 generally having a faster on-rate until the final value at 37° C. when H1L2 has a faster on-rate. However, a greater difference is seen when looking at off-rates, the two antibodies have similar off-rates at 15° C., 20° C., 25° C., but begin to diverge at 32° C. and 37° C., with the faster off-rate seen for H1L1. These changes are reflected in the overall equilibrium constant (which is a function of kd/ka), and indicate that the difference between H1L1 and H1L2 is mainly in the stability of the antibody/IL-18 complex as defined by the off-rate (kd).

d. Analysis of Binding of H1L1, H1L2, H1L3 and Chimeric 2C10 at 25° C. and 37° C.

These experiments were carried out as described above. Table 6 details the kinetic parameters obtained. The data shows that H1L2 is a better antibody than H1L1 in terms of binding as defined by the equilibrium constant KD both at 25° C. and 37° C., but the kinetic parameters show that at 25° C. H1L2 has a better on-rate (ka) than H1L1. At 37° C., the position is reversed indicating that the superior binding seen at 37° C. by H1L2 is more due to the off-rate (kd), indicating that the mutation that differentiates L2 from L1 bestows increased stability of the IL-18-antibody complex at higher temperatures.

TABLE 6

Kinetics of H1L1, H1L2, H1L3 and Chimeric 2C10 binding to Human IL-18 at 25° C. and 37° C.

| | Human IL18 at 25° C. | | | | Human IL18 at 37° C. | | |
|---|---|---|---|---|---|---|---|
| Antibody | Ka | Kd | KD (pM) | Antibody | Ka | Kd | KD (pM) |
| H1L1 | 2.49e6 | 7.94e−5 | 33.1 | H1L1 | 5.64e6 | 4.58e−4 | 94.3 |
| (n = 4) | (4.41e5) | (1.02e−5) | (9.3) | (n = 6) | (2.42e6) | (1.02e−4) | (39.6) |
| H1L2 | 2.88e6 | 4.32e−5 | 16.3 | H1L2 | 4.86e6 | 1.98e−4 | 46.0 |
| (n = 4) | (7.39e5) | (9.75e−6) | (7.0) | (n = 6) | (1.88e6) | (5.20e−5) | (18.8) |
| H1L3 | 2.36e6 | 4.53e−5 | 22.0 | H1L3 | 6.43e6 | 2.11e−4 | 64.8 |
| (n = 3) | (9.89e5) | (7.46e−6) | (9.9) | (n = 3) | (6.10e6) | (4.84e−5) | (57.3) |
| Chimera 2C10 | 6.88e6 | 5.22e−5 | 9.1 | Chimera 2C10 | 2.55e7 | 5.62e−4 | 22.9 |
| (n = 3) | (3.22e6) | (8.94e−5) | (4.7) | (n = 2) | (1.25e7) | (1.97e−4) | (3.5) |

The data is the mean of a number of separate data sets (n), the mean and standard deviation are shown, with the standard deviation in brackets. The values for the 25° C. and 37° C. runs for H1L1 and H1L2 obtained from analysis at five different temperatures are included in this data set.

e. Assessment of 2C10c Humanised Variants in IL-18 Binding ELISA

Figure 4A:
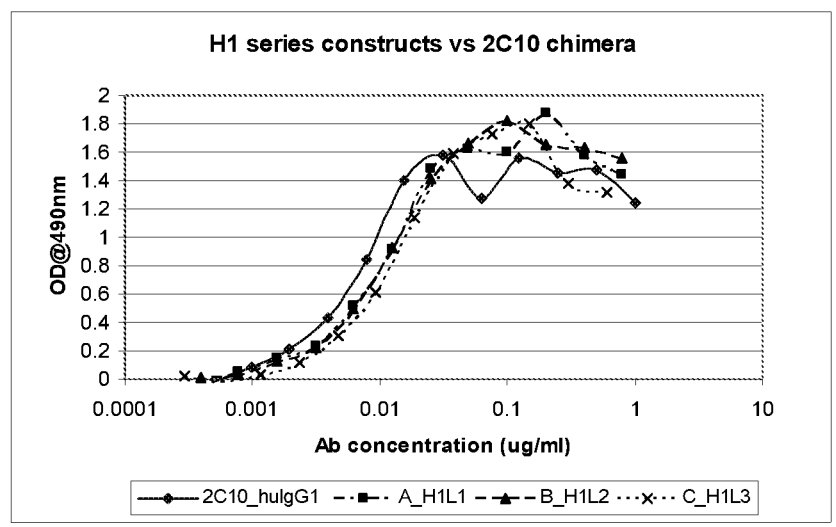
FIGS. 4A-4C show representative data from one experiment that generated the EC50 values illustrated in Table 7.
Figure 4B:
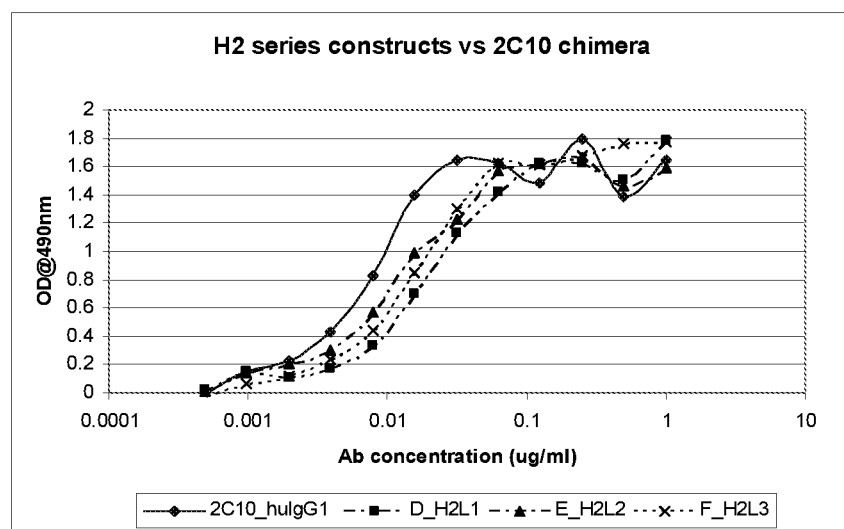
Figure 4C:
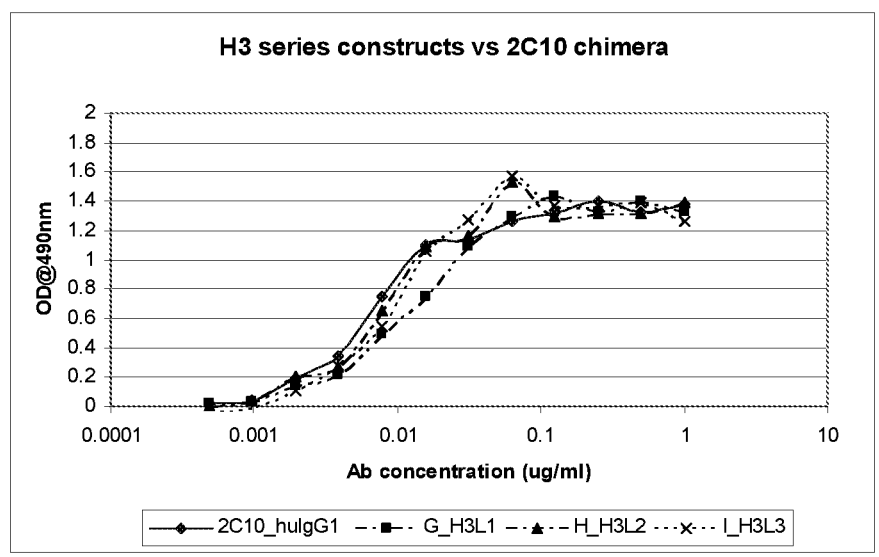

ELISA with all nine humanised variants was carried out at least 6 times using various batches of purified antibody preparation. FIGS. 4A-4C show representative data from one experiment which generated the EC50 value ranking illustrated in Table 7. Human IL-18 was immobilized on Nunc Maxisorp 96-well plates using 2.5 μg/ml of 16D10 (non-neutralising mouse monoclonal antibody) to capture 5 ng/ml of recombinant human IL-18. Anti-IL-18 humanised antibodies were added at various dilutions. Bound humanised antibodies were detected using anti-human IgG Fc specific peroxidase conjugate (Sigma A0170).

TABLE 7

Increasing EC50 values of humanised variants of 2C10 (expressed in [μg/ml]).

| | 2C10c | H3L2 | H3L3 | H1L1 | H1L2 | H1L3 | H2L2 | H3L1 | H2L3 | H2L1 |
|---|---|---|---|---|---|---|---|---|---|---|
| EC50* | 0.007 | 0.008 | 0.009 | 0.010 | 0.011 | 0.011 | 0.012 | 0.013 | 0.016 | 0.021 |

*All SE were between 0.001 and 0.002

Figure 5:
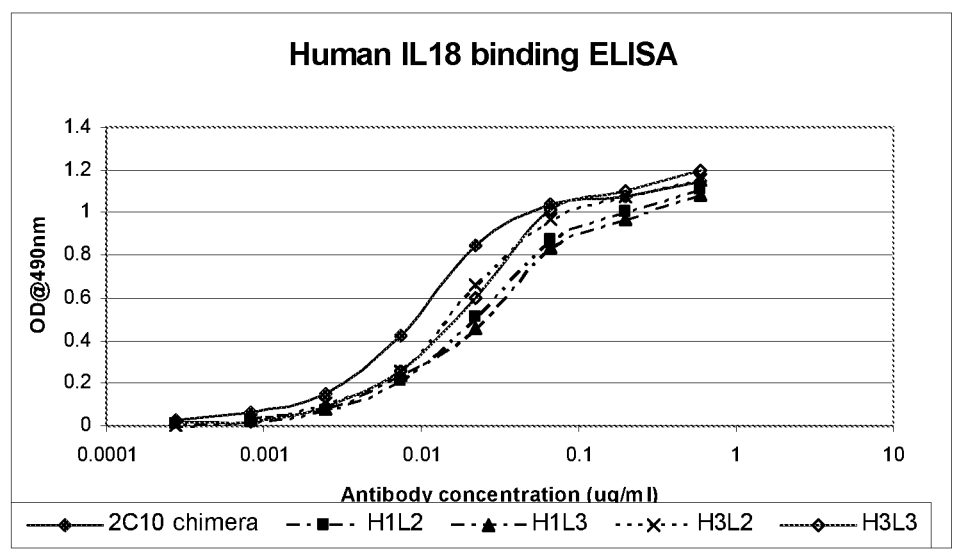
FIG. 5 shows EC50 values of four selected humanised variants binding to human IL-18.
Figure 6:
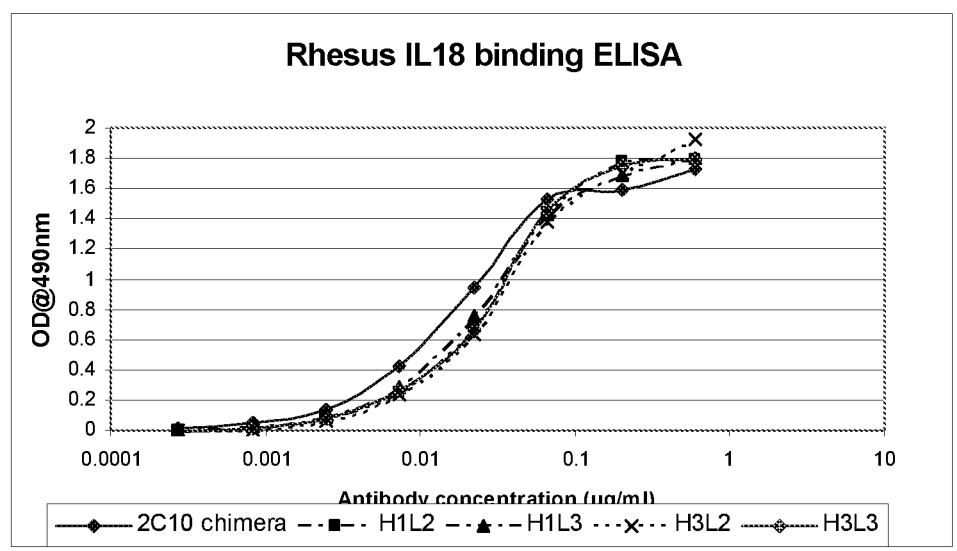
FIG. 6 shows EC50 values of four selected humanised variants binding to rhesus IL-18.

The potency of all variants appeared to be very close to 2C10 chimera, suggesting that humanisation had resulted in little loss of potency. Although the EC50 values generated by several repeats of these assays did generate a ranking of variants, ELISA alone did not allow a clear distinction between these variants (see Table 7 and FIGS. 4A-4C). A certain distinction of variants was achieved using Biacore™, (Examples 4a and 4b) which resulted in only 4 variants being examined closer in several independent repeat experiments using human and rhesus IL-18 (Table 8, FIGS. 5 [human] and 6 [rhesus]).

TABLE 8

EC50 values of six independent repeat experiments with four selected humanised variants for binding to human IL-18.

| | Exp. 1/1 | Exp. 1/2 | Exp. 2/1 | Exp. 2/2 | Exp. 3/1 | Exp. 3/2 | Average | SE |
|---|---|---|---|---|---|---|---|---|
| 2C10c | 0.015 | 0.016 | 0.013 | 0.011 | 0.020 | 0.020 | 0.0158 | 0.004 |
| H1L2 | 0.029 | 0.030 | 0.021 | 0.025 | 0.024 | 0.027 | 0.0260 | 0.003 |
| H1L3 | 0.027 | 0.025 | 0.029 | 0.028 | 0.029 | 0.027 | 0.0275 | 0.002 |
| H3L2 | 0.032 | 0.030 | 0.026 | 0.018 | 0.025 | 0.022 | 0.0255 | 0.005 |
| H3L3 | 0.035 | 0.028 | 0.018 | 0.021 | 0.025 | 0.025 | 0.0253 | 0.006 | f. Assessment of 2C10 Humanised H1 Variants in IL-18 Binding ELISA

ELISA was carried out with the three Humanised H1 variants; H1L1, H1 L2 and H1L3 to assess binding to human IL-18 at room temperature and at 37° C. in both human serum and in block solution (PBS 0.05% TWEEN with 1% BSA (w/v)). The Humanised antibody variants were immobilised on Nunc Maxisorp 96-well plates at 2.5 µg/ml. Capture of 5 ng/ml of recombinant human IL-18 was carried out either at room temperature or 37° C. in human serum or block solution. Anti-IL-18 mouse monoclonal antibody 16D10 was added. The bound mouse antibody was detected using anti-mouse kappa peroxidase conjugate (Serotec MCA 1291P). Representative EC50 values generated from the study data are illustrated in Table 9

TABLE 9

EC50 Values of 2C10 Humanised H1 variants at room temperature and at 37° C.

|  | EC50 (ng/ml) | Standard Error |
|---|---|---|
| Room temperature incubations In presence of serum: | | |
| 2C10 Chimera | 7.296 | 0.358 |
| H1L1 | 10.189 | 0.512 |
| H1L2 | 9.791 | 0.471 |
| H1L3 | 8.989 | 0.411 |
| In blocking buffer: | | |
| 2C10 Chimera | 3.814 | 0.068 |
| H1L1 | 3.315 | 0.136 |
| H1L2 | 3.552 | 0.079 |
| H1L3 | 3.790 | 0.133 |
| 37° C. incubations In presence of serum: | | |
| 2C10 Chimera | 10.140 | 1.254 |
| H1L1 | 12.069 | 0.740 |
| H1L2 | 9.791 | 0.471 |
| H1L3 | 11.438 | 1.861 |
| In blocking buffer: | | |
| 2C10 Chimera | 3.794 | 0.114 |
| H1L1 | 3.430 | 0.104 |
| H1L2 | 3.404 | 0.145 |
| H1L3 | 3.334 | 0.222 |

The potency of the three Humanised H1 variants is unaffected by changing the temperature at which the human IL-18 binding step is carried out, from room temperature to 37° C. in this assay. Lower binding signals are observed when the antibodies are present in human serum.

g. Assessment of Stability of Humanised H1 Variant Antibodies at 37° C.

Storage stability of the three Humanised H1 variants; H1L1, H1L2 and H1L3 was assessed over a time period of 14 days at 37° C. in both human serum and phosphate buffered saline. Antibodies were diluted to 50 µg/ml, stability was assessed by IL-18 binding ELISA following 37° C. incubation periods of 0, 1, 4, 6, 8, and 14 days. For the IL-18 binding ELISA, 16D10 (non-neutralising mouse monoclonal antibody) was immobilised on Nunc Maxisorp plates to capture 5 ng/ml recombinant human IL-18. The anti-IL-18 humanised antibodies sampled at different time points over the 37° C. time course incubation were added. Bound humanised antibodies were detected using anti-human IgG Fc specific peroxidase conjugate.

Prolonged exposure to a temperature of 37° C. for 0, 1, 4, 6, 8 and 14 days did not affect the binding potency of the Humanised H1 antibody variants based on their ability to bind to human IL-18 in this assay format.

Example 5: Binding of H1L2 to Human IL-18 in Presence of Synovial Fluid

Figure 7:
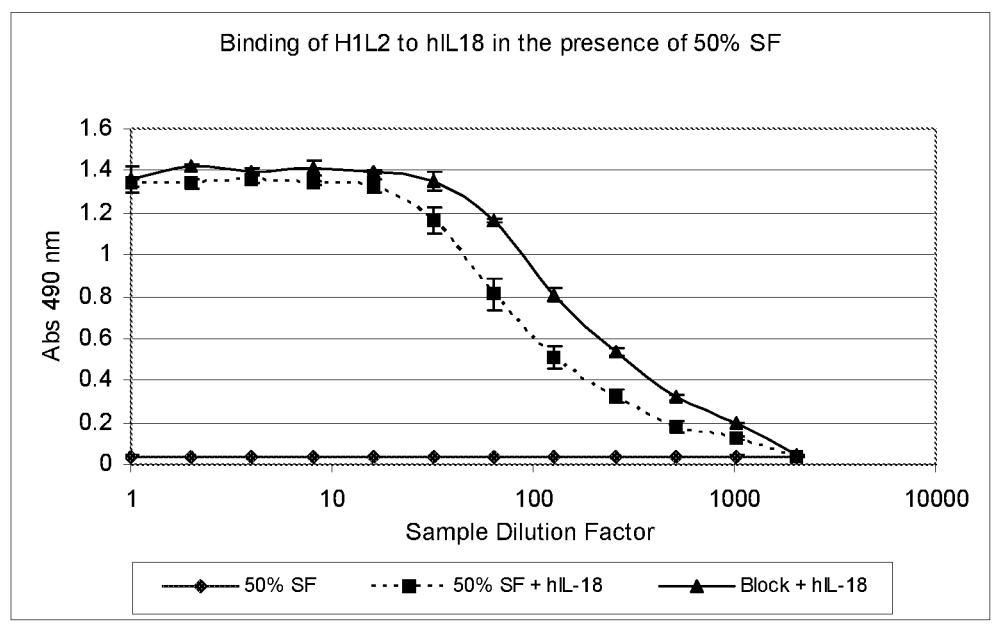
FIG. 7 shows binding of H1L2 to human IL-18 in the presence of 50% synovial fluid.

An ELISA was performed where 50% human synovial fluid was spiked with recombinant human IL-18 ranging from 500 ng/ml to 0 ng/ml. IL-18 contained in this solution was then applied to wells of a Maxisorp 96-well plate (Nunc) coated with the H1L2 antibody. Bound IL-18 was then detected through a biotinylated anti-IL-18 antibody (D045-6, MBL) and streptavidin-HRP. Titrating recombinant human IL-18 in 50% synovial fluid (SF) produced almost the same curve as titrating human recombinant IL-18 in buffer with only a slight shift in half maximal value. See FIG. 7. These results demonstrate the ability of the antibody to bind hIL-18, even in the presence of 50% human SF, which more closely mimics the binding environment the antibody will encounter in a therapeutic setting.

a. Binding to IL-18 in Presence of IL-18 Binding Protein (IL-18 bp)

Figure 8:
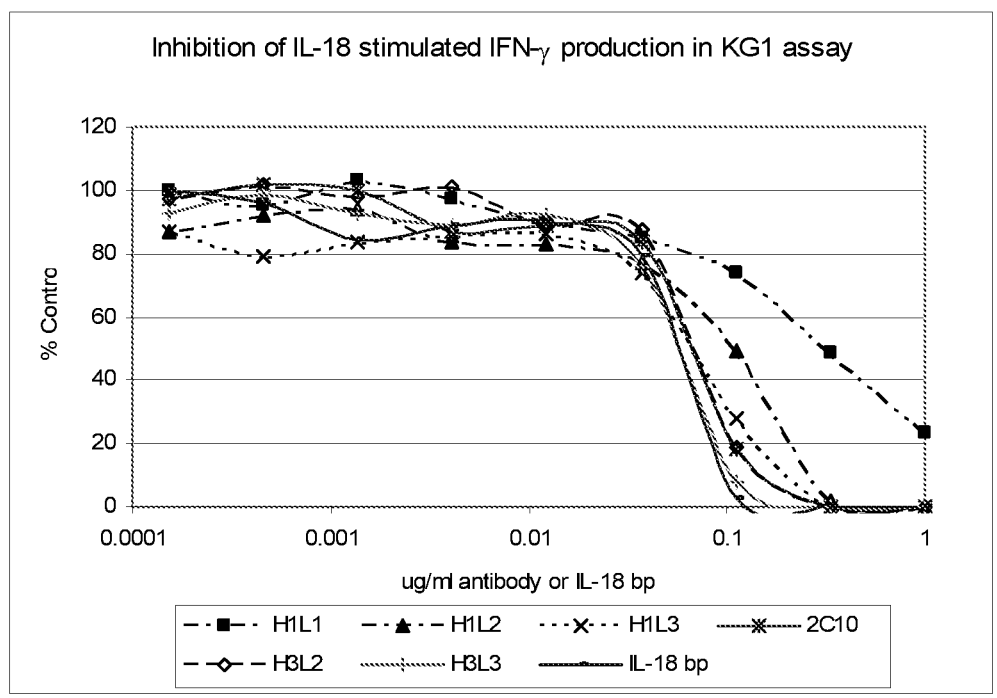
FIG. 8 shows the inhibition of IL-18 stimulated IFN-γ production in a KG1 assay.
Figure 9A:
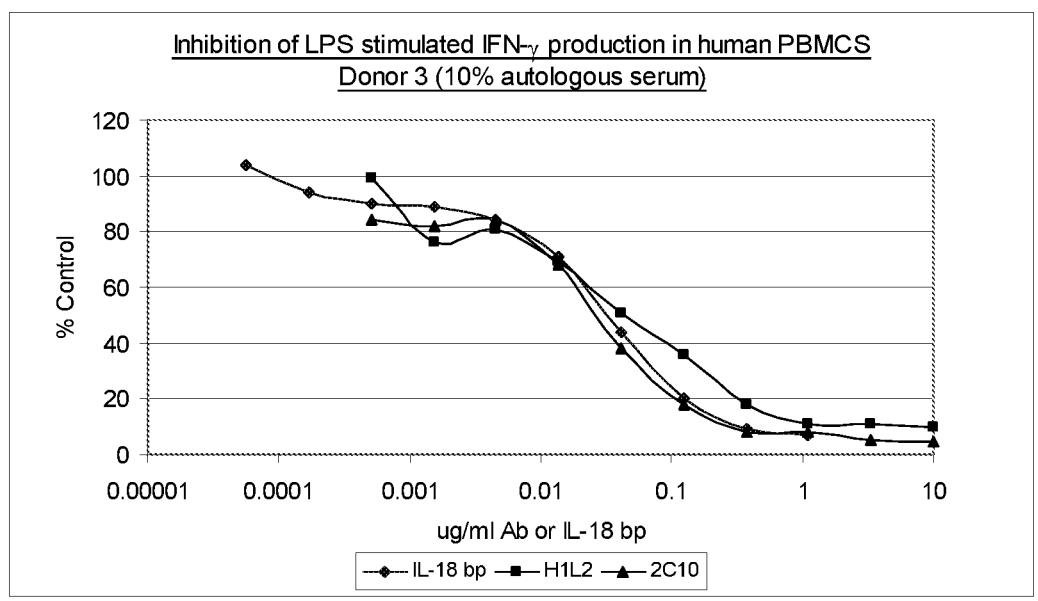
FIGS. 9A and 9B show the inhibition of LPS stimulated IFN-γ production in a human PBMCS donor in 10% and 25% autologous serum, respectively.
Figure 9B:
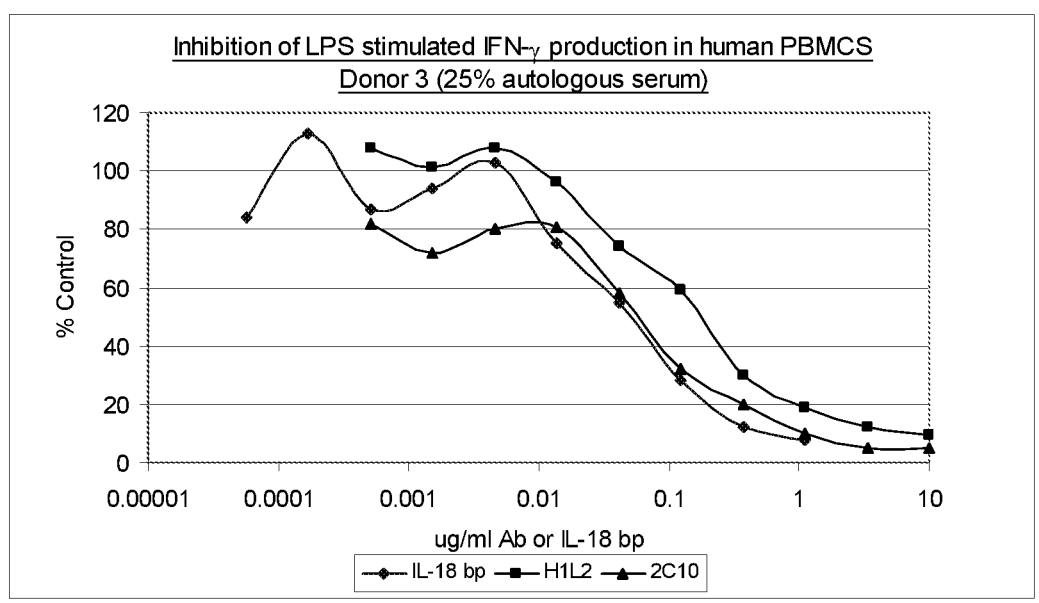

Biacore™ technology (Biacore™ 3000) and ELISA were used to determine whether H1L2 can still bind human IL-18 in the presence of human IL-18 bp. IL-18 bp has high affinity for IL-18 and acts as a natural inhibitor of IL-18 function (FIG. 8, FIGS. 9 A and B and, Tables 10 and 11).

b. Analysis by Biacore

Figure 10:
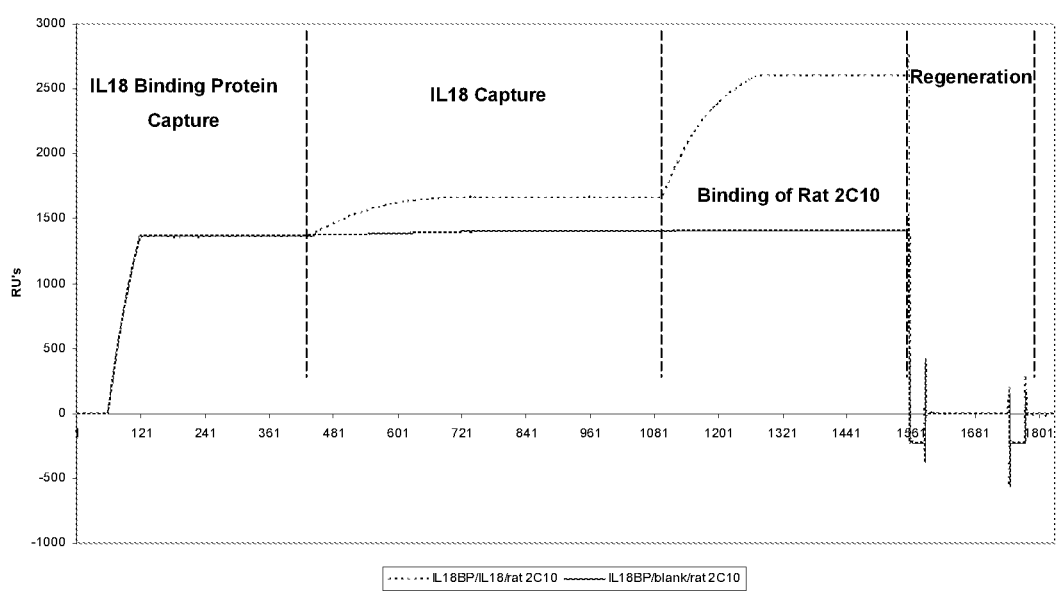
FIG. 10 shows 2C10 binding to hIL-18 captured by hIL-18-BP.

Briefly, Protein A was immobilised on a CM5 chip to a surface to a density of around 4000 resonance units (RU's) by primary amine coupling. Recombinant Fc-IL-18 binding protein (R&D Systems), was then passed over at a concentration of 3 µg/ml at a flow rate of 10 µl/minute for 1 minute; this resulted in the capture of around 1400 RU's of IL-18 binding protein. IL-18 was then passed over the captured IL-18 binding protein surface at a concentration of 30 nM, at a flow rate of 10 µl/minute for 5 minutes. After this the rat 2C10 parental antibody at a concentration of 10 nM was passed over the IL-18 binding protein/IL-18 surface for 3 minutes at a flow rate of 30 µl/minute for 3 minutes. Should the epitope recognized by 2C10 antibody on IL-18 interfere with the site of interaction for IL-18 binding protein then no binding signal should be seen. FIG. 10 demonstrates that 2C10 is bound to hIL-18 that, in turn, had been captured by hIL-18BP, indicating that the binding sites for 2C10 and hIL-18BP are not overlapping.

TABLE 10

Effect of IL-18BP on IFNγ secretion rheumatoid arthritis (RA) synovial cells

| Sample, IL-18BP status | Control | IL-12 | IL-18 | IL-12 + IL-18 |
|---|---|---|---|---|
| RA1 | | | | |
| − | ND | 0.63 | ND | 1.63 |
| + | ND | 0.29 | ND | 0.13 |
| RA2 | | | | |
| − | ND | 0.85 | ND | 0.70 |
| + | ND | 0.10 | ND | 0.10 |
| RA3 | | | | |
| − | ND | 1.06 | ND | 1.62 |
| + | ND | 0.32 | ND | 0.40 |

Kawashima, M. and Miossec, P., Arthritis & Rheumatism, Vol. 48, No. 3 (March 2003), pp 631-637 c. Analysis by ELISA

Figure 18A:
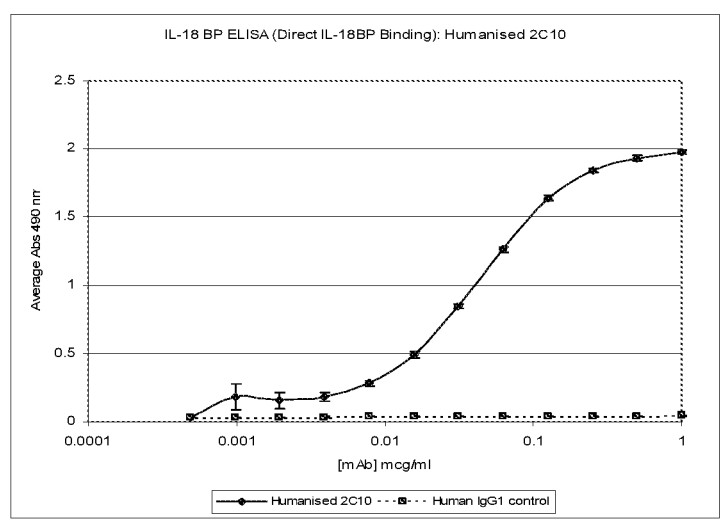
FIGS. 18A and 18B show the results of binding ELISAs using H1L2 and C10, respectively, to human IL-18-bound IL-18BP.
Figure 18B:
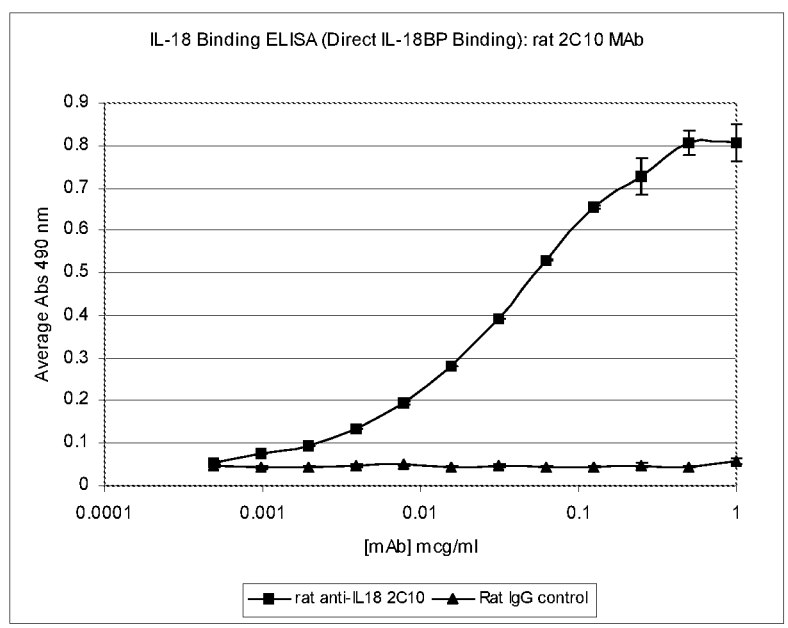

Binding of humanised H1L2 or 2C10 rat MAb to human IL-18 bound captured IL-18 bp was tested in direct binding ELISAs where recombinant human IL-18 bp-Fc fusion protein (R&D Systems #119-BP) was coated on Nunc Maxisorp plates at 0.5 µg/ml. Recombinant human IL-18 was added at 100 ng/ml in blocking buffer (PBS containing 1% w/v BSA). Purified antibodies were added at concentrations ranging from 0.5 ng/ml to 1 µg/ml. Bound antibody was detected with anti-human kappa light chain specific HRP conjugate (Sigma) or anti-rat IgG HRP. FIGS. 18A and 18B illustrate the results obtained.

Example 6: In Vitro Bioassay a. Activity of Humanised Constructs in Neutralizing IL-18 Stimulated IFN-γ Release in KG-1 Cell Line This assay measures the neutralising activity of antibody specific for IL-18 and is based on IL-18-mediated induction of IFNγ in KG-1 cells. KG-1 (ATCC # CCL-246) is a human myelomonocytic cell line that constitutively expresses functional IL-18 receptor and, therefore, responds to exogenous IL-18 stimulation.

Figure 11:
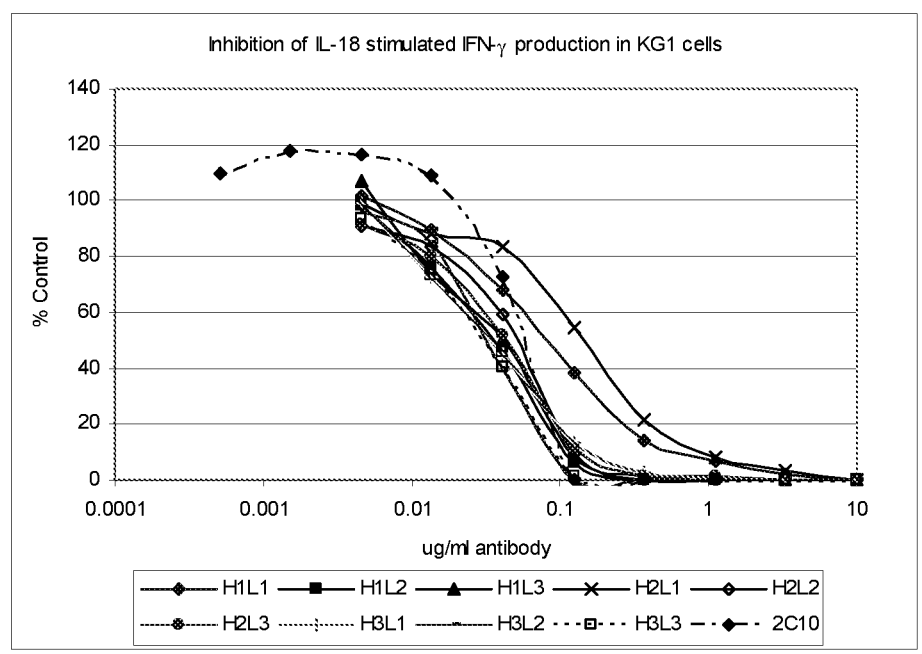
FIG. 11 shows the ability of the nine humanised variants to inhibit human IL-18-stimulated IFN-γ release in KG1 cells.

All nine humanised variants were assessed for their ability to inhibit human IL-18 stimulated IFN-γ release in KG-1 cells (Table 11 and FIG. 11).

TABLE 11

IC50 values for neutralisation of recombinant human IL-18 in KG-1 bioassay using all nine humanised variants.

| Antibody | IC50 |
|---|---|
| H1L1 | 0.071 |
| H1L2 | 0.033 |
| H1L3 | 0.027 |
| H2L1 | 0.145 |
| H2L2 | 0.054 |
| H2L3 | 0.046 |
| H3L1 | 0.027 |
| H3L2 | 0.035 |
| H3L3 | 0.034 |
| 2C10(1) | 0.042 |
| 2C10(2) | 0.039 |

At least 6 further repeat experiments were performed on four preferred humanised variants which had shown best affinity for recombinant human and rhesus IL-18 based on Biacore™ analysis. FIG. 8 illustrates a representative result for the four preferred humanised variants and for H1L1, and Table 12 summarises the results of these assays all carried out with the same protein batch material derived from CHOe1a cells.

TABLE 12

IC50 values for neutralisation of recombinant human IL-18 in KG-1 bioassay using 4 or 5 selected humanised variants.

| | Mean 2C10 IC50 | (H1L1) | (H1L2) | (H1L3) | (H3L2) | (H3L3) | IL-18 bp |
|---|---|---|---|---|---|---|---|
| Expt. 1 | 0.046 | n.d. | 0.062 | 0.064 | 0.064 | 0.057 | n.d. |
| Expt. 2 | no fit | n.d. | no fit | no fit | no fit | no fit | n.d. |
| Expt. 3 Plate 1 | 0.074 | n.d. | 0.109 | 0.144 | 0.090 | 0.091 | n.d. |
| Expt. 3 Plate 2 | 0.075 | n.d. | 0.173 | 0.156 | 0.128 | 0.115 | n.d. |
| Expt. 4 | 0.017 | 0.091 | 0.017 | 0.044 | no fit | 0.016 | No fit |
| Expt. 5 (Est. EC80) | 0.075 | 0.757 | 0.122 | 0.085 | 0.072 | 0.056 | 0.054 |
| Expt. 5 (Est. EC50) | 0.044 | 0.180 | 0.047 | 0.046 | 0.039 | 0.038 | 0.034 |
| Expt. 6 (Est. EC80) | no fit | 0.078 | 0.023 | 0.021 | no fit | 0.013 | 0.007 |
| Expt. 6 (Est. EC50) | 0.020 | 0.069 | 0.019 | 0.019 | 0.015 | 0.016 | 0.01 |

In cases where H1L1 was compared to other humanised variants, H1L1 demonstrated lower potency compared to the other four humanised constructs tested and also compared to 2C10 parental MAb.

Further analysis was performed with the four preferred monoclonal antibodies, which were compared for the capacity of inhibiting IL-18 stimulated INFγ release by KG-1 cells: 2C10 and the humanised variants derived from 2C10 (H1L1, H1L2 and H1L3). The KG-1 bioassay was performed in 96-well plates by incubating 50 ng/ml of recombinant human IL-18 and various concentrations of the antibodies specific for IL-18 (ranging from 2 µg/ml to 7.8 ng/ml, in double dilutions) or a negative isotype control (Synagis, anti-RSV antibody) for 1 hour at 37° C. and 5% $CO_2$, followed by the addition of $3.10^5$ KG-1 cells per well. The plates were finally incubated for 20-24 hrs at 37° C., 5% $CO_2$. The supernatant was harvested and the IFNγ production was determined using a commercial human IFNγ ELISA kit (Biosource AHC4432; AHC4539).

Three experiments have been performed. The results for the inhibition of IL-18 stimulated IFNγ production were normalized to the negative control. The statistical analysis aimed to gain an IC50 estimate for each mAb on each experiment following adjustment for any Synagis response. The IC50 estimates were then statistically analyzed to produce an overall estimate of IC50 for each mAb with a 95% confidence interval (i.e., statistically plausible range). Each humanised variant was finally compared back to 2C10 using Dunnett's test.

Figure 12:
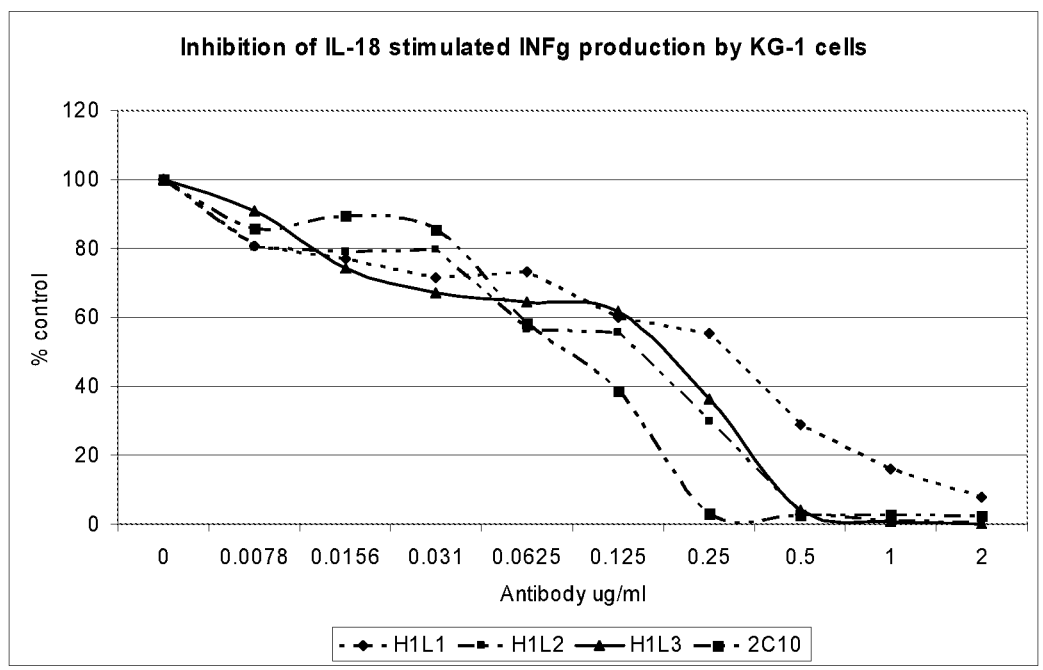
FIG. 12 shows inhibition of IL-18 stimulated IFN-γ production by the H1 variants and 2C10 in KG1 cells.
Figure 13:
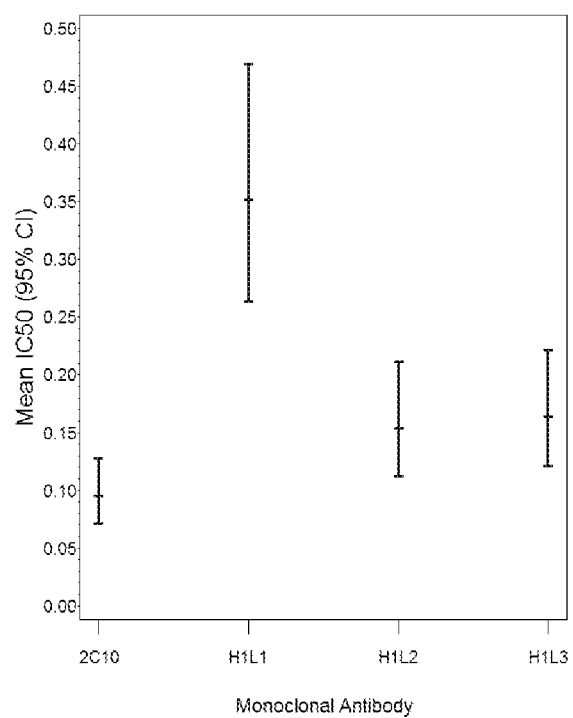
FIG. 13 shows IC50 data for the H1 variants with a 95% confidence interval.

FIG. 12 illustrates a representative experiment. Table 13 and FIG. 13 show an overall estimate of IC50 for each monoclonal antibody with a 95% confidence interval and % change from rat 2C10 with p values and confidence intervals.

TABLE 13

IC50 values for neutralisation of IL-18 stimulated INFγ production in KG-1 bioassay.

| Monoclonal Antibody | mean IC50 μg/ml (95% CI) | % change vs 2C10 (95% CI) | Dunnett p value |
|---|---|---|---|
| 2C10 | 0.095 (0.071, 0.127) | — | — |
| H1L1 | 0.352 (0.264, 0.470) | 269.4 (117.2, 528.2) | 0.0001 |
| H1L2 | 0.154 (0.112, 0.211) | 61.5 (−7.6, 182.0) | 0.0968 |
| H1L3 | 0.164 (0.121, 0.221) | 71.6 (−0.4, 195.8) | 0.0519 |

H1L1 is statistically significantly less potent than 2C10 ($p<0.001$).
The other humanised variants are not significantly different from 2C10, although the comparison for H1L3 versus 2C10 is borderline.

b. Activity of H1L2 in Neutralizing IFN-γ Release in Stimulate Human PBMCs

Figure 14:
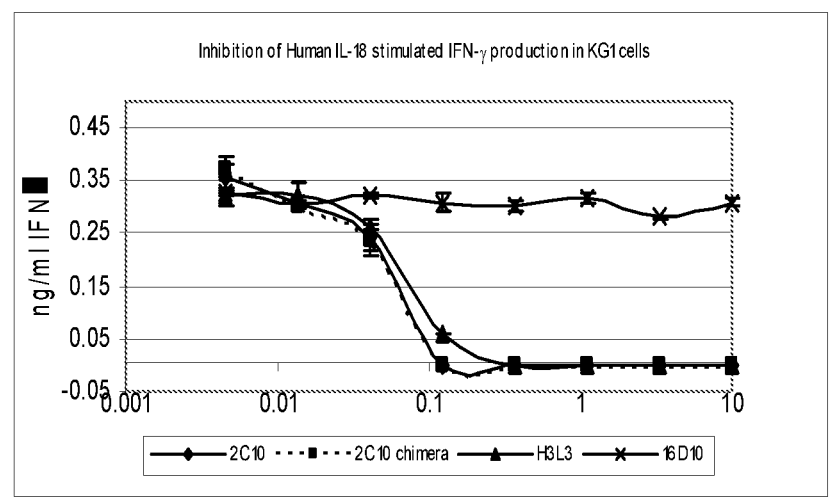
FIG. 14 shows inhibition of human IL-18 stimulated IFN-γ production in KG1 cells.

Human PBMC from three donors were stimulated with recombinant human IL-18 and anti-CD3 antibody and the effect of adding a dilution series of the four selected humanised antibody variants studied. For each donor, parental 2C10 antibody and IL-18 bp was included for comparison. For two of the three donors IL-18 and anti-CD3 stimulation was unsuccessful and no IFN-γ was detected. For the remaining donor, results were very variable at low concentrations but a complete inhibition of IL-18 induced IFN-γ production could be achieved by adding various anti-IL-18 antibodies including humanised variants. See FIG. 14.

Experiments were also carried out with LPS-stimulated human PBMCs, which results in IL-18 production and associated IFNγ release. IFNγ production was induced by LPS in a concentration-dependent manner and adding 2C10 parental monoclonal antibody at a fixed concentration of 1 μg/ml completely inhibited this stimulation, indicating that the effect is IL-18 mediated and that endogenous IL-18 can be neutralized (data not shown). This could also be demonstrated in whole blood, but the inhibition effect with 2C10, although dose dependent, was less evident (data not shown). FIG. 9 illustrates results from an experiment with 3 independent donors and inhibition with parental rat monoclonal 2C10, H1 L2 and IL-18 bp. Donors 1 and 3 gave similar results, whereas donor 2 showed no IFNγ release on stimulation with LPS (not shown). IL-18 mediated IFNγ release can be completely inhibited in the presence of 10% or 25% of human serum by adding >1 μg/ml antibody or IL-18 bp. Inhibition can already be observed at 10 ng/ml and above and IC50 values for this inhibition in presence of 10% or 25% human serum are shown in Table 14.

TABLE 14

IC50 values for inhibition of LPS-stimulated IFNγ release caused by endogenous IL-18 neutralisation using 2C10, H1L2, or IL-18bp in the presence of human serum.

| | IL-18bp | H1L2 | 2C10 |
|---|---|---|---|
| Donor 1 10% serum | 0.024 | 0.102 | 0.023 |
| Donor 1 25% serum | 0.064 | 0.113 | 0.069 |
| Donor 3 10% serum | 0.032 | 0.042 | 0.033 |
| Donor 3 25% serum | 0.046 | 0.108 | 0.086 | c. Summary of Binding to IL-18 Orthologues

Binding of antibody with IL-18 from other species was examined using ELISA and Biacore and also KG-1 cell bioassay. This was initially performed using parental 2C10 and chimeric 2C10c for rhesus/cynomolgus IL-18, but was repeated with some of the humanised variants. Parental 2C10 was tested for binding to pig, mouse and rat IL-18 and the 4 best humanised variants were tested for binding to rhesus/cynomolgus and dog IL-18 using Biacore and ELISA. KG-1 bioassay was carried out with rhesus/cynomolgus IL-18 and three monoclonal antibodies, 2C10 chimeric and representatively for the humanised variants, H3L3. Given the similarity of all humanised variants this is likely to be representative for other variants generated including H1L2 (see Table 15, FIG. 8).

TABLE 15

Overview of orthologue binding of 2C10 parental rat MAb, rat-human chimera 2C10c and selected pool of 4 humanised variants

| | Rhesus/Cynomolgus IL-18 | Dog IL-18 | Mouse & Rat IL-18 | Pig IL-18 |
|---|---|---|---|---|
| 2C10 rat MAb | ELISA (+)<br>KG-1 (+) | ELISA (−) | ND | ND |
| 2C10 chimeric (rat/human) | ELISA (+)<br>KG-1 (+)<br>Biacore ™ (+) | ELISA (−)<br>Biacore ™ (−) | ELISA (−)<br>Biacore ™ (−) | ELISA (−)<br>Biacore ™ (−) |
| Humanised (H1L2, H1L3, H3L1, H3L3) | ELISA (+)<br>KG-1 (+) only H3L3 tested<br>Biacore ™ (+) | ELISA (−) | ELISA (−) | ELISA (−) |

ND not determined;
+ detectable binding

Example 7: Circular Dichroism and Thermal Denaturation Studies of IL-18 Antibodies Circular dichroism (CD) studies were used to study the secondary structural changes of the IL-18 antibodies as a function of temperature, especially from 25° C. to 37° C. Thermal denaturation studies of these same antibodies were conducted to determine their thermal stability and their melting temperatures (Tm.)

CD Method:

CD spectra were acquired on a Applied Photophysics Chirascan spectrometer scanning from 180 nm-280 nm in steps of 0.5 nm and bandwidth of 1 nm. The acquisition time per point was 5 s. The samples were diluted to ~0.2 mg/ml in PBS and placed in a 1 mm pathlength cell. Spectra of each protein were taken with the thermostatic bath set at 4° C., 25° C. and 37° C. The actual temperatures of the samples were determined by a probe placed within the body of the liquid within the cell and were within ~3° C. of the set temperature.

Tm Method:

All proteins were diluted to 0.2 mg/ml in 1:1000 Sypro orange in phosphate buffered saline (PBS) solution. The fluorescence emission was measured @ 620 nm (excitation @490 nm) using a Bioneer Exicycler instrument at every 0.5° C. interval whilst the sample temperature was ramped from 10° C. to 95° C. waiting 10 s at each temperature point.

The denaturation curves were fitted to a standard melting isotherm using Grafit. As expected, comparison of the shape of the CD spectra from all four antibodies showed their structure to be highly beta sheet and of essentially the same architecture. In the temperature range from 4° C.-37° C. the three antibodies:

H1L1
H1L2
H1L3 show no significant changes in their secondary structure, as revealed by CD. However, the 2C10 antibody chimera did show a slight decrease in structure in this temperature range. This is consistent with thermal stability trend given in Table 16 below.

TABLE 16

Thermal denaturation of IL-18 antibodies

| Antibody | H1L1 | H1L2 | H1L3 | chimera |
|---|---|---|---|---|
| Tm | 73° C. | 70° C. | 67° C. | 65° C. |

Tm = denaturation/melting temperature

H1L1, H1L2 and H1L3 are clearly stable far beyond 37° C. with no signs of any denaturation at body temperature. Their difference in thermal stability is therefore unlikely to confer any differential advantages at normal body and ambient temperatures.

What is claimed is:

1. A method of neutralizing IL-18 in an IL-18 mediated disease or disorder in a human in need thereof, said method comprising administering to the human a therapeutically effective amount of an anti-IL1,8 antibody or antigen binding fragment thereof, wherein the anti-IL18 antibody comprises complementarity determining regions (CDRs) selected from the group consisting of:
   CDRH1 as set forth in SEQ ID NO: 1;
   CDRH2 as set forth in SEQ ID NO: 2;
   CDRH3 as set forth in SEQ ID NO: 3;
   CDRL1 as set forth in SEQ ID NO: 4;
   CDRL2 as set forth in SEQ ID NO: 5; and
   CDRL3 as set forth in SEQ ID NO: 6.

2. The method of claim 1, wherein the anti-IL18 antibody comprises a heavy chain comprising an amino acid sequence selected from the group consisting of: SEQ ID NO: 11, SEQ ID NO: 19, and SEQ ID NO: 23.

3. The method of claim 1, wherein the anti-IL18 antibody comprises a light chain comprising an amino acid sequence selected from the group consisting of: SEQ ID NO: 15, SEQ ID NO: 27, and SEQ ID NO: 31.

4. The method of claim 1, wherein the anti-IL18 antibody comprises a heavy chain comprising an amino acid sequence selected from the group consisting of: SEQ ID NO: 11, SEQ ID NO: 19, and SEQ ID NO: 23, and a light chain comprising an amino acid sequence selected from the group consisting of: SEQ ID NO: 15, SEQ ID NO: 27, and SEQ ID NO: 31.

5. The method of claim 1, wherein the anti-IL18 antibody comprises a heavy chain comprising an amino acid sequence selected from the group consisting of: SEQ ID NO: 11, SEQ ID NO: 19, SEQ ID NO: 23, SEQ ID NO: 9, SEQ ID NO: 17, and SEQ ID NO: 21.

6. The method of claim 1, wherein the anti-IL 18 antibody comprises a light chain comprising an amino acid sequence selected from the group consisting of: SEQ ID NO: 15, SEQ ID NO: 27, SEQ ID NO: 31, SEQ ID NO: 13, SEQ ID NO: 25, and SEQ ID NO: 29.

7. The method of claim 1, wherein the anti-IL18 antibody comprises a heavy chain comprising an amino acid sequence selected from the group consisting of: SEQ ID NO: 11, SEQ ID NO: 19, SEQ ID NO: 23, SEQ ID NO: 9, SEQ ID NO: 17, and SEQ ID NO: 21, and a light chain comprising an amino acid sequence selected from the group consisting of: SEQ ID NO: 15, SEQ ID NO: 27, SEQ ID NO: 31, SEQ ID NO: 13, SEQ ID NO: 25, and SEQ II) NO: 29.

8. The method of claim 1, wherein the anti-IL18 antibody comprises a heavy chain comprising the amino acid sequence shown in SEQ ID NO: 11, and a light chain comprising the amino acid sequence shown in SEQ ID NO: 15.

9. The method of claim 1, wherein the anti-IL18 antibody comprises a heavy chain comprising the amino acid sequence shown in SEQ ID NO: 11 and a light chain comprising the amino acid sequence shown in SEQ ID NO: 15.

10. The method of claim 1, wherein the anti-IL18 antibody comprises a heavy chain comprising the amino acid sequence shown in SEQ ID NO: 9 and a light chain comprising the amino acid sequence shown in SEQ ID NO: 13.

11. The method of claim 1, wherein the anti-IL18 antibody is humanized.

12. The method of claim 1, wherein the disease or disorder is selected from the group consisting of: inflammatory bowel disease (IBD), multiple sclerosis, rheumatoid arthritis, Type 1 diabetes, and psoriasis.

13. The method of claim 1, wherein the disease or disorder is inflammatory bowel disease (IBD).

* * * * *